United States Patent
Audonnet et al.

(10) Patent No.: US 7,078,388 B2
(45) Date of Patent: Jul. 18, 2006

(54) DNA VACCINES FOR FARM ANIMALS, IN PARTICULAR BOVINES AND PORCINES

(75) Inventors: Jean-Christophe Francis Audonnet, Lyons (FR); Laurent Bernard Fischer, Sainte Foy les Lyon (FR); Simona Barzu-Le-Roux, Lentilly (FR)

(73) Assignee: Merial, Lyons (FR)

( * ) Notice: Subject to any disclaimer, the term of this patent is extended or adjusted under 35 U.S.C. 154(b) by 639 days.

(21) Appl. No.: 09/760,574

(22) Filed: Jan. 16, 2001

(65) Prior Publication Data

US 2002/0058021 A1    May 16, 2002

Related U.S. Application Data

(60) Provisional application No. 60/193,126, filed on Mar. 30, 2000.

(30) Foreign Application Priority Data

Jan. 21, 2000    (FR) .................................. 00 00798

(51) Int. Cl.
*A61K 48/00*    (2006.01)
(52) U.S. Cl. .................. 514/44; 424/211.1; 424/278.1; 424/283.1; 424/813; 435/320.1; 536/23.72
(58) Field of Classification Search ................ 514/44; 424/93.1, 450, 211.1, 278.1, 283.1, 813; 430/325.1; 435/455, 320.1; 536/23.72
See application file for complete search history.

(56) References Cited

U.S. PATENT DOCUMENTS

| | | | |
|---|---|---|---|
| 4,946,787 A | | 8/1990 | Eppstein et al. |
| 5,106,733 A | * | 4/1992 | Baker et al. ............... 435/69.5 |
| 5,459,127 A | | 10/1995 | Felgner et al. |
| 5,545,412 A | | 8/1996 | Eppstein et al. |
| 5,548,412 A | | 8/1996 | Minamizawa et al. |
| 5,580,859 A | | 12/1996 | Felgner et al. |
| 5,620,896 A | | 4/1997 | Herrmann et al. |
| 5,643,578 A | | 7/1997 | Robinson et al. |
| 5,703,055 A | | 12/1997 | Felgner et al. |
| 5,705,385 A | | 1/1998 | Bally et al. |
| 5,719,131 A | * | 2/1998 | Harris et al. .................. 514/44 |
| 5,846,946 A | | 12/1998 | Huebner et al. |
| 5,910,488 A | | 6/1999 | Nabel et al. |
| 6,019,980 A | | 2/2000 | Li et al. |
| 6,187,759 B1 | | 2/2001 | Tarpey et al. |
| 6,287,856 B1 | | 9/2001 | Poet et al. |
| 6,376,473 B1 | * | 4/2002 | Audonnet et al. ............ 514/44 |
| 6,451,770 B1 | | 9/2002 | Rijsewijk et al. |
| 6,586,409 B1 | * | 7/2003 | Wheeler ....................... 514/44 |

FOREIGN PATENT DOCUMENTS

| | | |
|---|---|---|
| EP | 737 750 | 3/1990 |
| WO | WO 90 11092 | 10/1990 |
| WO | WO 92 05255 | 4/1992 |
| WO | WO 93 19183 | 9/1993 |
| WO | WO 94/01133 | 1/1994 |
| WO | WO 94 21797 | 9/1994 |
| WO | WO 94/27435 | 12/1994 |
| WO | WO 96/40945 * | 6/1995 |
| WO | WO 95/20660 | 8/1995 |
| WO | WO 96 06619 | 3/1996 |
| WO | WO 98/02179 * | 7/1996 |
| WO | WO 96/34109 | 10/1996 |
| WO | WO 96/40945 | 12/1996 |
| WO | WO 97 23502 | 7/1997 |
| WO | WO 97/40163 | 10/1997 |
| WO | WO 97/41236 | 11/1997 |
| WO | WO 98/03200 | 1/1998 |
| WO | WO 98/03660 | 1/1998 |
| WO | WO 98/40499 | 9/1998 |
| WO | WO 00 24428 | 5/2000 |
| WO | WO 01/52888 A2 | 7/2001 |

OTHER PUBLICATIONS

Anthony H. Choi et al., VIROLOGY, 250, pp. 230-240 (1998).*
Geraldine Taylor et al., Journal of General Virology, (1997), 78, pp. 3195-3206.*

(Continued)

*Primary Examiner*—Anne-Marie Falk
*Assistant Examiner*—John Eric Angell
(74) *Attorney, Agent, or Firm*—Frommer Lawrence & Haug LLP; Thomas J. Kowalski; Judy Jarecki-Black

(57) ABSTRACT

DNA vaccine against a pathogen affecting farm animals, in particular bovines or porcines, comprising a plasmid containing a nucleotide sequence encoding an immunogen of a pathogen of the animal species considered, under conditions allowing the in vivo expression of this sequence, and a cationic lipid containing a quaternary ammonium salt, of formula

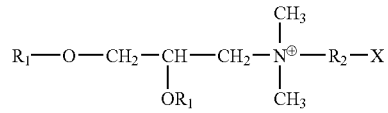

in which R1 is a saturated or unsaturated linear aliphatic radical having 12 to 18 carbon atoms, R2 is another aliphatic radical containing 2 or 3 carbon atoms, and X a hydroxyl or amine group, this lipid being preferably DMRIE.

35 Claims, 2 Drawing Sheets

OTHER PUBLICATIONS

Figure 1:
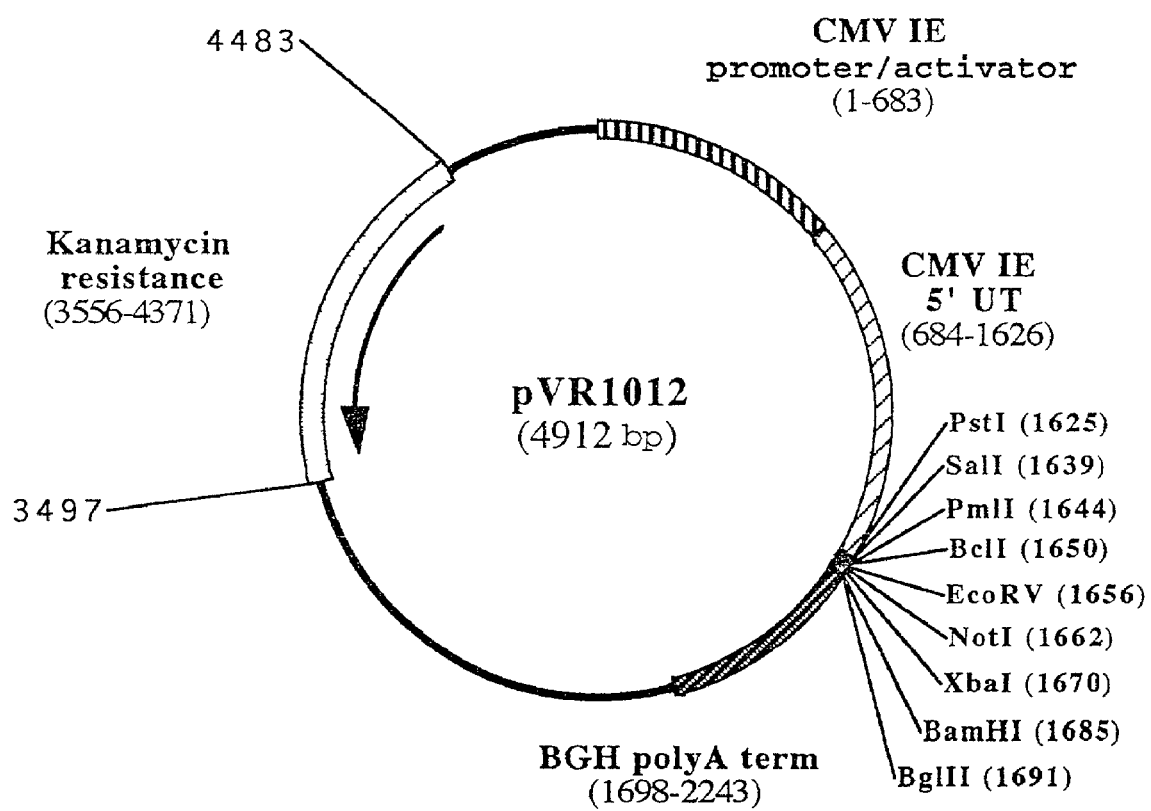

Zhiquan Xiang et al., IMMUNITY, vol. 2, pp. 129-135.*

Klavinskis L.S. et al. Intranasal immunization with plasmid DNA-lipid complexes elicits mucosol immunity in the female genital and rectal tracts. (J. Immunol. vol. 162, No. 1, pp. 254-262; Jan. 1, 1999).*

Gao Yi et al., "Truncated Bvine Herpesvirus-1 Glycoprotein I (gpI) Initiates a Protective Local Immune Response in its Natural Host" Vaccine, GB, Butterworth Scientific Guilford; vol. 12, No. 2, 1994, pp. 145-152.

Wheeler, C.J. et al., "Converting an Alcohol 1-40 to an Amine in a Cationic Lipid Dramatically Alters to Co-Lipid Requirement, Cellular Transfection Activity and the Ultrastructure of DNA-Cytofectin Complexes"; BioChimica et BioPhysica Acta, NL, Amsterdam; vol. 1280, No. 1, 1996, pp. 1-11.

Felgner J.H. et al., "Enhanced Gene Delivery and Mechanism Studies with a Novel Series of Cationic Lipid Formulations"; Journal of Biological Chemistry, U.S., American Society of Biological Chemists, Baltimore, MD, vol. 269, No. 4, Jan. 28, 1994, pp. 2550-2561.

Li Xiaomao et al, "Protection Against Respiratory Syncytial Virus Infection by DNA Immunization"; Journal of Experimental Medicine, Tokyo, JP, vol. 188, No. 4, Aug. 17, 1998, pp. 681-688.

Cox, GJM, et al. "Bovine Herpesirus 1: Immune Responses in Mice and Cattle Injected with Plasmid DNA" J. Virol 1993, vol. 67, No. 9:5664-5667.

Hartikka, J, et al. "An Improved Plamid DNA Expression Vector for Direct Injection into Skeletal Muscle" Human Gene Therapy 1996, vol. 7:1205-1217.

Manthorpe, M., et al. "Gene Therapy by Intramuscular Injection of Plasmid DNA" Studies on Firefly Luciferase Gene Expression in Mice Human Gene Therapy 1993, vol. 4:419-431.

Bourne, N., et al. "DNA Immunization against Experimental Genital Herpes Simplex Virus Infection" The Journal of Infectious Diseases 1996, vol. 173:800-807.

Ertl, H.C.J. and Xiang, Z.Q. "Genetic Immunization" Viral Immunology 1996, vol. 9, No. 1:1-9.

van Drunen Little-van den Hurk, S. et al., "Intradermal immunization with a bovine herpesvirus—1 DNA vaccine induces protective immunity in cattle" Journal of General Virology 1998, vol. 79:831-839.

Donnelly, J.J., et al., "Immunization with DNA" Journal of Immunological Methods 1994, vol. 176:145-152.

van Rooij, E.M.A., et al., "Effect of vaccination route and composition of DNA vaccine on the induction of protective immunity against pseudorabies infection in pigs" Veterinary Immunology and Immunopathology 1998, vol. 66:113-126.

Ulmer, J.B., et al., "Protective immunity by intramuscular injection of low doses of influenza virus DNA vaccines" Vaccine 1994, vol. 12, No. 16:1541-1544, (Abstract) Abstract only considered.

Andrew, M.E., et al., "Protection of pigs against classical swine fever with DNA-delivered gp55" Vaccine 2000, vol. 18:1932-1938.

Ulmer, J. B., et al., "Heterologous Protection Against Influenza by Injection of DNA Encoding a Viral Protein" Science 1993, vol. 259:1745-1749.

Xiang, Z.Q., et al., "Vaccination with a Plasmid Vector Carrying the Rabies Virus Glycoprotein Gene Induces Protective Immunity against Rabies Virus" Virology 1994, vol. 199:132-140.

Jenkins, M., et al., "Serum and colostrum antibody responses induced by jet-injection of sheep with DNA encodeing a *Cryptosporidium parvum* antigen" Vaccine 1995, vol. 13, No. 17:1658-1664.

Fynan, E.F. et al., "DNA vaccines: Protective immunizations by parenteral, mucosal, and gene-gun inoculations" Proceedings of the National Academy of Sciences, USA 1993, vol. 90:11478-11482.

Robinson, H.L. et al., "Protection against a lethal influenza virus challenge by immunization with a haemagglutinin-expressing plasmid DNA" Vaccine 1993, vol. 11, No. 9:957-960.

Zhu, N. et al., "Systemic Gene Expression After Intravenous DNA Delivery into Adult Mice" Science 1993, vol. 261:209-211.

Sixt, N. et al., "Canine Distemper Virus DNA Vaccination Induces Humoral and Cellular Immunity and Protects against a Lethal Intracerebral Challenge" Journal of Virology 1998, vol. 72, No. 11:8472-8476.

Ban, E.M. et al., "Mucosal immunization with DNA encoding influenza hemagglutinin" Vaccine 1997, vol. 15, No. 8:811-813. (Abstract).

Etchart, N. et al., "Class I-restricted CTL induction by mucosal immunization with naked DNA encoding measles virus haemagglutinin" Journal of General Virology 1997, vol. 78:1577-1580.

Gregoriadis, G. "Genetic Vaccines: Strategies for Optimization" Pharmaceutical Research 1998, vol. 15, No. 5:661-670.

Ishii, N. et al., "Cationic Liposomes Are a Strong Adjuvant for a DNA Vaccine of Human Immunodeficiency Virus Type 1" AIDS Research and Human Retroviruses 1997, vol. 13, No. 16:1421-1428.

Haddad, D. et al., "Comparative study of DNA-based immunization vectors: effect of secretion signals on the antibody responses in mice" FEMS Immunology and Medical Microbiology 1997, vol. 18:193-202.

Gregoriadis, G. et al., "Liposome-mediated DNA vaccination" FEBS Letters 1997, vol. 402:107-110.

Xiang, Z. and Ertl, H.C.J. "Manipulation of the Immune Response to a Plasmid-Encoded Viral Antigen by Coinoculation with Plasmids Expressing Cytokines" Immunity 1995, vol. 2:129-135.

Choi, A.H.C. et al., "Particle-Bombardment-Mediated DNA Vaccination with Rotavirus VP4 or VP7 Induces High Levels of Serum Rotavirus IgG but Fails to Protect Mice against Challenge" Virology 1998, vol. 250:230-240.

Xu, L. et al., "Immunization for Ebola virus infection" Nature Medicine 1998, vol. 4, No. 1:37-42.

Behr, J.P. "Gene Transfer with Synthetic Cationic Amphiphiles: Prospects for Gene Therapy" Bioconjugate Chemistry 1994, vol. 5, No. 5:382-389.

Roberto Bei et al., Journal of Immunotherapy, 1998 "The Use of a Cationic Liposome Formulation (DOTAP) Mixed with a Recombinant Tumor-Associated Antigen to Induce Immune Responses and Protective Immunity in Mice".

R. Braun et al., Journal of General Virology 1998, "Compatibility of plasmids expressing different antigens in a single DNA vaccine formulation".

Yoshifumi Watanabe et al., J. Bircher 1994 "Highly Efficient Transfection into Primary Cultured Mouse Hepatocytes by Use of Cation-Liposomes: An Application for Immunization".

Nash Blood 1991 (abstract).

NP Restifo et al., Gene Therapy 2000, "The Promise of Nucleic Acid Vaccines".

Eiichi Okada et al., Journal of Immunology 1997, "Intranasal Immunization of a DNA Vaccine IL-12-and Granulocyte-Macrophage Colony-Stimulating Factor (GM-CSF)-Expressing Plasmids in Liposomes Induces Strong Mucosal and Cell-Mediated Immune Responses Against HIV-1 Antigens".

Masayuki Yokoyama et al., FEM Immunology and Medical Microbiology 1996, "DNA Immunization: Effects of Vehicle and Route of Administration on the Induction of Protective Antiviral Immunity".

Linda S. Klavinskis et al., J. Immunol 1999, "Intranasal Immunization with Plasmid DNA-Lipid Complexes Elicits Mucosal Immunity in the Female Genital and Rectal Tracts".

Jae Ho Cho et al., Vaccine 1999, Enhanced Cellular Immunity to Hepatitis C Virus Nonstructural Proteins by Codelivery of Granulocyte Macrophage-Colony Stimulating Factor Gene in Intramuscular DNA Immunization.

Michael D. Macklin et al., Journal of Virology, Feb. 1998, p. 1491-1496, "Immunization of Pigs with a Particle-Mediated DNA Vaccine to Influenza a Virus Protects against Challenge with Homologous Virus".

Van Rooij et al., Veterinary Immunology and Immunopathology, 2000, "A DNA Vaccine Coding for Glycoprotein B of Pseudorabies Virus Induces Cell-Mediated Immunity in Pigs and Reduces Virus Excretions Early After Infection".

Bart L. Haagmans et al., Vaccine, 1999, "Vaccination of Pigs Against Pseudorabies Virus with Plasmid DNA Encoding Glycoprotein D".

Boroushan Pirzadeh et al., Journal of General Virology, 1998, "Immune Response in Pigs Vaccinated with Plasmid DNA Encoding ORF5 of Porcine Reproductive and Respiratory Syndrome Virus".

C. Somasundaram et al., Veterinary Immunology and Immunopathology, 1999, "Enhanced Protective Response and Immuno-Adjuvant Effects of Porcine GM-CSF on DNA Vaccination of Pigs against Aujeszky's Disease Virus".

Jeong-Im Sin et al., Vaccine, vol. 15, 1997, "Protective Immunity Against Heterologous Challenge with Encephalomyocarditis Virus by VP1 DNA Vaccination: Effect of Coinjection with a Granulocyte-Macrophage Colony Stimulating Factor Gene".

S. Inumaru et al., Immunology and Cell Biology, 1995, XP-000946635, "cDNA Cloning of Porcine Granulocyte-Macrophage Colony-Stimulating Factor".

Colin J. McInnes et al., Gene, 1991, XP-002148815, "Cloning and Expression of a cDNA Encoding Ovine Granulocyte-Macrophage Colony-Stimulating Factor".

Lorne A. Babiuk et al., Veterinary Immunology and Immunopathology, 2000, "Nucleic Acid Vaccines: Research Tool or Commercial Reality".

Jan Schultz et al., Intervirology 2000, "Update on Antiviral DNA Vaccine Research" (1998-2000).

Parker et al., XP-002153286, "Cancer Gene Therapy" 1996.

Michael J. McCluskie et al., Molecular Medicine, 1999, "Route and Method of Delivery of DNA Vaccine Influence Immune Responses in Mice and Non-Human Primates".

L.A. Babiuk et al., "DNA Immunization with Bovine Herpesvirus-1 Genes" 1995.

Weiwen Jiang et al., Vaccine, vol. 16, 1998, "Nucleic Acid Immunization Protects Dogs against Challenge with Virulent Canine Parvovirus".

Masashi Sakaguchi et al., Vaccine, vol. 14, 1996, "Protection of Chickens from Newcastle Disease by Vaccination with a Linear Plasmid DNA Expressing the F Protein of Newcastle Disease Virus".

Jon A. Norman et al., Vaccine, vol. 15, 1997, "Development of Improved Vectors for DNA-Based Immunization and other Gene Therapy Applications".

K. M. Ruitenberg et al., Vaccine, vol. 17, 1999, pp. 237-244, "DNA-Mediated Immunization with Glycoprotein D of Equine Herpesvirus 1 (EHV-1) in a Murine Model of EHV-1 Respiratory Infection".

Ann Hwee Lee et al., Vaccine, vol. 17, 1999, pp. 473-479, "DNA Inoculations with HIV-1 Recombinant Genomes that Express Cytokine Genes Enhance HIV-1 Specific Immune Responses".

Seung Woo Lee et al., Vaccine, vol. 17, 1999, pp. 490-496, "IL-6 Induces Long-term Protective Immunity against a lethal challenge of Influenza Virus".

Elanchezhiyan Manickan et al., Critical Reviews in Immunology, 1997, "DNA Vaccines—A Modern Gimmick or a Boon to Vaccinology".

P. Jeffrey Lewis et al., Vaccine, vol. 15, pp. 861-864, 1997, "Polynucleotide Vaccines in Animals: Enhancing and Modulating Responses".

Nikolaus Osterrieder et al., Virology, 1995, Protection against EHV-1 Challenge Infection in the Murine Model after Vaccination with Various Formulations of Recombinant Glycoprotein gp 14 (gB).

Zhi Quan Xiang et al., Virology, 1995, pp. 569-579, XP-002029171 "Immune Responses to Nucleic Acid Vaccines to Rabies Virus".

J.M. Furze et al., Virology, 1997, vol. 231, pp. 48-58, "Antigenically Distinct G Glycoproteins of BRSV Strains Share a High Degree of Genetic Homogeneity".

Naik, S. and Shaila, MS. "Characterization of membrane-bound and membrane anchor-less forms of hemagglutinin glycoprotein of Rinderpest virus expressed by baculovirus recombinants" Virus Genes 1997, vol. 14, No. 2:95-104. (Abstract).

Philip J. Wiilson, et al., Tissue Reaction and Immunity in Swine Immunized with *Actinobacillus pleuropneumoniae* Vaccines, Veterinary Infectious Disease Organization, No. 192, pp. 299-305, 1995.

Robert Edelman, "An Update on Vaccine Adjuvants in Clinical Trial", Research and Human Retroviruses, vol. 8, No. 8, pp. 1409-1411, 1992.

Margaret Juliana McElrath, "Selection of Potent Immunological Adjuvants for Vaccine Contruction", Cancer Biology, vol. 6, pp. 375-385, 1995.

J. Aucouturier, et al., "Adjuvants Designed for Veterinary and Human Vaccines", Vaccine, vol. 19, pp. 2666-2672, 2001.

Iain J. East, et al., "Adjuvants for New Veterinary Vaccines", Progress in Vaccinology, vol. 4, pp. 1-28, 1993.

Amnon Altman, et al., "Immunomodifiers in Vaccines", Advances in Veterinary Science and Comparative Medicine, vol. 33, pp. 301-343, 1989.

Van Drunen Littel-van den Hurk, "Strategies for improved formulation and delivery of DNA vaccines to veterinary target species", Immunological Reviews 2004, vol. 199:113-125.

Sergio Harpin, David J. Hurley, Majambu Mbikey, Brian Talbot and Youssef Elazhary, "Vaccination of cattle with a DNA plasmid encoding the bovine viral diarrhean virus major glycoprotein E2", Journal of General Virology 1999, vol. 80:3137-3144.

\* cited by examiner

Plasmid pVR1012

Plasmid pAB110

DNA VACCINES FOR FARM ANIMALS, IN PARTICULAR BOVINES AND PORCINES

This application claims the benefit of provisional application Ser. No. 60/193,126 filed Mar. 30, 2000.

The present invention relates to improved DNA vaccines for farm animals, in particular bovines and porcines.

The use of deoxyribonucleic acid (DNA) molecules for vaccination has been known since the beginning of the 1990s (Wolf et al. Science 1990. 247. 1465–1468). This vaccination technique induces cellular and humoral immunity after in vivo transfection of cells of the subject to be vaccinated with DNA or RNA molecules encoding immunologically active proteins.

A DNA vaccine is composed of at least one plasmid which may be expressed by the cellular machinery of the subject to be vaccinated and of a pharmaceutically acceptable vehicle or excipient. The nucleotide sequence of this plasmid encodes, inter alia, one or more immunogens, such as proteins or glycoproteins capable of inducing, in the subject to be vaccinated, a cellular immune response (mobilization of the T lymphocytes) and a humoral immune response (stimulation of the production of antibodies specifically directed against the immunogen) (Davis H. L. Current Opinion Biotech. 1997. 8. 635–640).

All the immunogens derived from a pathogen are not antigens which are naturally sufficiently effective for inducing an optimum protective immune response in the animal to be vaccinated. It is therefore necessary to improve the immune response.

Various routes of administration of the DNA vaccine have been proposed (intraperitoneal, intravenous, intramuscular, subcutaneous, intradermal, mucosal, and the like). Various means of administration have also been proposed, in particular gold particles coated with DNA and projected so as to penetrate into the cells of the skin of the subject to be vaccinated (Tang et al. Nature 1992. 356. 152–154) and the liquid jet injectors which make it possible to transfect both skin cells and cells of the underlying tissues (Furth et al. Analytical Bioch. 1992. 205. 365–368).

Chemical compounds have been used for the in vitro transfection of DNA:

A/—cationic lipids.

The cationic lipids are themselves divided into four subgroups.

1) The cationic lipids containing quaternary ammonium salts, such as for example DOTMA (dioleoyloxypropyl-trimethylammonium, produced by Gibco under the name Lipofectine), DOTAP (trimethyl-2,3-(octadec-9-eneoyloxy)-1-propaneammonium; Gregoriadis et al. FEBS Letters 1997. 402. 107–110), DMRIE (N-(2-hydroxyethyl)-N,N-dimethyl-2,3-bis(tetradecyloxy)-1-propaneammonium; WO-A-9634109), DLRIE (N-(2-hydroxyethyl)-N,N-dimethyl-2,3-bis(dodecyloxy)-1-propaneammonium; Felgner et al. Ann. N Y Acad. Sci. 1995. 772. 126–139).

These cationic lipids containing quaternary ammonium salts may be combined or otherwise with an additional neutral lipid, such as DOPC (dioleoylphosphatidylcholine) or DOPE (dioleoylphosphatidylethanolamine) (J. P. Behr, Bioconjugate Chemistry 1994. 5. 382–389).

2) The lipoamines, such as for example DOGS (dioctadecylamidoglycylspermine, produced by Promega under the name Transfectam; Abdallah et al. Biol. Cell. 1995. 85. 1–7), DC-Chol (dimethylaminoethane-carbamoyl-cholesterol; Gao and Huang, Biochem. Biophys. Res. Commun. 1991. 179. 280–285), BGSC (bis-guanidine-spermidine-cholesterol), BGTC (bis-guanidine-tren-cholesterol) (Vigneron et al. Proc. Natl. Acad. Sci. USA 1996. 93. 9682–9686).

3) The cationic lipids containing quaternary ammonium salts and lipoamines, such as for example DOSPA (N,N-dimethyl-N-(2-(sperminecarboxamido)ethyl)-2,3-bis(dioleoyloxy)-1-propaneimidium pentahydro-chloride, marketed by Gibco under the name LipofectAmine®; Hawley-Nelson et al. Focus 1993. 15. 73–79), GAP-DLRIE (N-(3-aminopropyl)-N,N-dimethyl-2,3-bis(dodecyloxy)-1-propaneammonium; Wheeler et al. Proc. Natl. Acad. Sci. USA 1996. 93. 11454–11459; Norman et al. Vaccine 1997. 15. 801–803).

4) The lipids containing amidine salts, such as for example ADPDE, ADODE (Ruysschaert et al. Biochem. Biophys. Res. Commun. 1994. 203. 1622–1628).

B/—the polymers, such as for example SuperFect™ (molecules of activated dendrimers, produced by Qiagen; Xu et al. Mol. Genet. Metab. 1998. 64. 193–197), and C/—the biochemical agents, such as for example toxins, in particular cholera toxins.

Some of these compounds have also been used in the formulation of DNA vaccines with more than mitigated results. Knowledge in the field of in vitro transfection is not transposable to DNA vaccination where the final objective is to ensure a protective immune reaction. Negative effects on the induction of an effective immune protection have even been observed with compounds known to promote transfection in vitro. Some formulation chemical compounds are toxic at high doses for the transfected cells.

In the work by Etchart (Etchart et al. J. Gen. Virol. 1997. 78. 1577–1580), the use of DOTAP did not have an adjuvant effect during the administration of the DNA vaccine by the intranasal route, whereas it had an adjuvant effect by the oral route. DOTAP has also been used in DNA vaccines encoding the influenza virus hemagglutinin (HA) on the mouse model which were administered by the intranasal route (Ban et al. Vaccine 1997. 15. 811–813), but the addition of DOTAP inhibited the immune response. The use of DC-Chol or of DOTAP/DOPE in DNA vaccines encoding the hepatitis B virus surface protein (S) on the mouse model which were administered by the intramuscular route made it possible to increase the antibody response, whereas the use of Lipofectine (or DOTMA) did not increase this response (Gregoriadis et al. FEBS Letters 1997. 402. 107–110). DC-Chol/DOPE has also been used in DNA vaccines against the human immunodeficiency virus (HIV, Env protein) on the mouse model, whose administration by the intramuscular route induced a more effective immune response, whereas the administration by the subcutaneous or intradermal route did not increase it (Ishii et al. AIDS Res. Hum. Retro. 1997. 13. 1421–1428).

The addition of certain cytokines, in particular interleukins or interferons, can make it possible to enhance the immune response induced in particular by DNA vaccines. Each cytokine triggers a reaction which is specific to it and orients the immune response to a greater or lesser degree towards a cellular response or towards a humoral response (Pasquini et al. Immunol. Cell. Biol. 1997. 75. 397–401; Kim et al. J. Interferon Cytokine Res. 1999. 19. 77–84). The adjuvant effects of a cytokine obtained from a given species are not necessarily the same if the immune context varies, in particular if this cytokine is administered to another species, therefore in a heterologous immune system. The addition of cytokine may also have no adjuvant effect, or may even result in a reversal of the effect sought, that is to say a reduction or an inhibition of the immune response. Thus, a DNA vaccine encoding a single chain of an immunoglobulin fused with GM-CSF does not increase the immune response, whereas direct administration of this fusion protein to mice is effective, in the same way as is the administration of a fusion protein consisting of Fv and of the cytokine IL-1beta or the administration of a DNA vaccine encoding the latter fusion protein (Hakim et al. J. Immunol. 1996. 157. 5503–5511). The use of plasmids co-expressing the cytokine IL-2 and the hepatitis B virus envelope protein in a fused or nonfused conformation results in an increase in the humoral and cellular immune responses (Chow et al. J. Virol. 1997. 71. 169–78). However, the use of a bicistronic plasmid encoding the human acquired immunodeficiency virus (HIV-1) glycoprotein gp120 and the cytokine IL-2 induced a lower specific anti-gp120 immune response than that obtained by the use of a monocistronic plasmid encoding only gp120 (Barouch et al. J. Immunol 1998. 161. 1875–1882). The co-injection, into mice, of two expression vectors, one coding for the rabies virus G glycoprotein, the other for murine GM-CSF stimulates the activity of the B and T lymphocytes, whereas the co-injection with a plasmid encoding gamma-interferon (in place of murine GM-CSF) results in a decrease in the immune response (Xiang et al. Immunity 1995. 2. 129–135).

Certain modifications in the antigens, such as deletions of part of the nucleotide sequence encoding the antigen, insertions of a DNA fragment into the nucleotide sequence encoding the antigen or into non-translated regions upstream or downstream, can also enhance the efficacy of DNA vaccines, in particular by enhancing the level of expression of the antigen or its presentation.

However, in practice, manipulations on the nucleotide sequence encoding the antigen may bring about a reduction or loss of the initial immunological activity. Thus, the deletion of the transmembrane domain from the gene encoding the rabies virus G antigen reduced the level of protection induced in the mouse model after administration by the intramuscular route of a DNA vaccine encoding this modified antigen (Xiang et al. Virol. 1995. 209. 569). The deletion of the transmembrane domain from the gene encoding the bovine herpesvirus (BHV) gD glycoprotein did not make it possible to increase the antibody response and induced only a partial protection in bovines vaccinated by the intramuscular route (van Drunen Little-van den Hurk et al. J. Gen. Virol. 1998. 79. 831–839). The humoral and cellular immune responses and the protection conferred are identical in guinea pigs challenged after having been immunized with the aid of either a DNA vaccine encoding the Ebola virus GP glycoprotein, or of a DNA vaccine encoding this GP glycoprotein but in a secreted form (Xu et al. Nature Medicine 1998. 4. 37–42).

The insertion of the signal sequence of the human tissue plasminogen activator (tPA) into the gene encoding the malaria Pf332 antigen did not make it possible to increase the antibody response in mice vaccinated by the intramuscular route (Haddad et al. FEMS 1997. 18. 193–202). The addition, in phase, of a tPA sequence to the gene encoding the murine rotavirus VP7 antigen also did not make it possible to increase the antibody response in mice vaccinated by the intradermal route, whereas the fusion protein consisting of the VP4 antigen and tPA allowed this increase, but without inducing an effective protection (Choi et al. Virology 1998. 250. 230–240).

The modifications carried out on the nucleotide sequence of one antigen cannot in general be directly transposed to another antigen, because antigens do not always have the same structural arrangements.

The applicant has as objective the enhancement of the efficacy of DNA vaccination. Its objective is in particular to obtain a better immune response and in particular an effective protection in farm animals, in particular bovines and porcines, by DNA vaccinations.

The applicant has as objective the production of improved DNA vaccines which induce an effective and protective immune response against the bovine herpesvirus type 1 (BHV-1) also called infectious bovine rhinotrachitis (IBR), the bovine respiratory syncitial virus (BRSV), the mucosal disease virus or bovine pestivirus type 1 or type 2 (bovine viral diarrhea virus or BVDV-1 and BVDV-2), the parainfluenza virus type 3 (bPI-3) in bovines.

The applicant has as objective the production of improved DNA vaccines which induce an effective and protective immune response comprising at least one valency selected from the group consisting of porcine herpesvirus or Aujeszky's disease (pseudorabies virus or PRV), the porcine reproductive respiratory syndrome virus (or PRRSV), the swine influenza virus (or SIV), the conventional hog cholera virus (or HCV), parvoviruses in porcines.

The applicant also has as objective the production of improved DNA vaccines which make it possible to obtain effective and protective immune protection in bovines, comprising at least one valency selected from the group consisting of the BHV-1, BRSV, BVDV, bPI-3 and rabies viruses.

The subject of the invention is improved DNA vaccines which make it possible to obtain effective protection against at least one pathogen which infects farm, in particular bovines and porcines. The DNA vaccine is improved: either by its formulation, or by the addition of GM-CSF, or by the optimization of the antigen(s), or by combinations of these solutions.

Preferably, the DNA vaccine is improved by its formulation, and optionally either by the addition of GM-CSF, or by the optimization of the antigen(s), or finally by the addition of GM-CSF and by the optimization of the antigen(s).

By definition, the DNA vaccine comprises, as active ingredient, a plasmid encoding and expressing a gene or gene fragment e.g. epitope. The term plasmid covers a DNA transcription unit comprising a polynucleotide sequence comprising the sequence of the gene to be expressed and the elements necessary for its expression in vivo. The circular plasmid form, supercoiled or otherwise, is preferred. The linear form also falls within the scope of this invention.

Each plasmid comprises a promoter capable of ensuring, in the host cells, the expression of the gene inserted under its control. It is in general a strong eukaryotic promoter and in particular a cytomegalovirus early promoter CMV-IE, of human or murine origin, or optionally of other origin such as rat or guinea pig. More generally, the promoter is either of viral origin or of cellular origin. As a viral promoter other than CMV-IE, there may be mentioned the SV40 virus early or late promoter or the Rous Sarcoma virus LTR promoter. It may also be a promoter the virus from which the gene is derived, for example the promoter specific to the gene. As cellular promoter, there may be mentioned the promoter of a cytoskeleton gene, such as for example the desmin promoter, or alternatively the actin promoter. When several genes are present in the same plasmid, they may be provided in the same transcription unit or in several different units.

According to a first mode, the DNA vaccines according to the invention are formulated by adding, as adjuvant, cationic lipids containing a quaternary ammonium salt of formula:

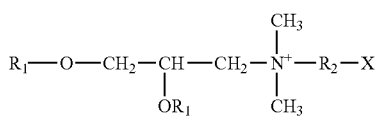

in which $R_1$ is a saturated or unsaturated linear aliphatic radical having 12 to 18 carbon atoms, $R_2$ is another aliphatic radical containing 2 or 3 carbon atoms, and X a hydroxyl or amine group.

Preferably, this is DMRIE (N-(2-hydroxyethyl)-N,N-dimethyl-2,3-bis(tetradecyloxy)-1-propanammonium; WO-A-9634109), preferably combined with a neutral lipid, in particular, DOPE (dioleoyl-phosphatidylethanolamine), to form DMRIE-DOPE.

The subject of the present invention is therefore a DNA vaccine against at least one pathogen affecting farm animals, in particular bovines or porcines, comprising at least one plasmid containing at least one nucleotide sequence encoding an immunogen of a pathogen of the animal species considered, under conditions allowing the in vivo expression of this sequence, and a cationic lipid containing a quaternary ammonium salt, in particular DMRIE, preferably combined with DOPE.

Preferably, the recombinant vector is mixed with this adjuvant immediately before use and it is preferable, before its administration to the animal, to allow the mixture thus prepared to form a complex, for example for a period ranging from 10 to 60 minutes, in particular of the order of 30 minutes.

When DOPE is present, the DMRIE:DOPE molar ratio preferably ranges from 95:5 to 5:95, and is more particularly 1:1.

The plasmid:DMRIE or DMRIE-DOPE adjuvant weight ratio may range in particular from 50:1 to 1:10, in particular from 10:1 to 1:5, preferably from 1:1 to 1:2.

According to a second mode, GM-CSF (granulocyte macrophage-colony stimulating factor; Clark S. C. et al. Science 1987. 230. 1229; Grant S. M. et al. Drugs 1992. 53. 516) is added to the vaccines according to the invention; this may be carried out by incorporating GM-CSF protein directly into the vaccinal composition or preferably by inserting the nucleotide sequence encoding GM-CSF into an expression vector under conditions allowing its expression in vivo. As expression vector, the use of a plasmid, e.g. the plasmid containing the nucleotide sequence encoding the antigen(s) of interest or another plasmid, is preferred. The choice of GM-CSF is preferably made according to the animal species to be vaccinated; thus, for bovines, bovine GM-CSF is used; for pigs, it is porcine GM-CSF.

According to a third mode, the nucleotide sequence(s) encoding the immunogen are in an optimized form. Optimization is understood to mean any modification of the nucleotide sequence, in particular which manifests itself at least by a higher level of expression of this nucleotide sequence, and/or by an increase in the stability of the messenger RNA encoding this antigen, and/or by the triggered secretion of this antigen into the extracellular medium, and having as direct or indirect consequence an increase in the immune response induced.

In the present invention, the optimization of the antigen of interest preferably consists in the deletion of the fragment of the nucleotide sequence encoding the transmembrane domain of the antigen of interest (deletion is understood to mean the complete deletion or a partial deletion sufficient for the transmembrane domain to no longer, or no longer substantially, be functional), and/or in the addition, in frame, of a nucleotide sequence encoding the tPA (Montgomery et al. Cell. Mol. Biol. 1997. 43. 285–292; Harris et al. Mol. Biol. Med 1986. 3. 279–292) signal, and/or in the insertion of a stabilizing intron upstream of the gene to be expressed. The deletion of the DNA fragment encoding the transmembrane domain of the antigen of interest promotes the secretion, into the extracellular medium, of the antigens thus truncated and thus increases the possibilities of their coming into contact with the cells of the immune system. The insertion of the nucleotide sequence encoding the tPA signal facilitates the translatability of the messenger RNA to which the tPA signal is joined, and thus increases the level of expression of this messenger RNA and therefore the production of antigens. The tPA signal also plays a role in the secretion of the antigen synthesized.

Other nucleotide sequences encoding signal peptides may be used, in particular those for the signal peptide of melittin obtained from bees (Sisk W. P. et al., 1994, J. Virol., 68, 766–775).

The insertion of a stabilizing intron into the gene encoding the antigen of interest avoids the aberrant splicings of its messenger RNA and maintains the physical integrity of the latter.

Preferably, the tPA signal is of human origin. The nucleotide sequence of the human tPA signal is accessible from the GenBank database under the accession number NM_000930. Preferably, the intron is intron II of the rabbit beta-globin gene (van Ooyen et al. Science 1979. 206. 337–344), whose nucleotide sequence is accessible from the GenBank database under the accession number V00882 and designated by a reference under intron No. 2.

The subject of the present invention is an improved DNA vaccine capable of inducing an effective and protective immune response in bovines against infectious bovine rhinotrachitis (IBR).

The virus responsible for infectious bovine rhinotrachitis is a bovine herpesvirus type 1 (BHV-1), a member of the Alphaherpesvirinae family (Babiuk L. A. et al., 1996, Vet. Microbiol., 53, 31–42). Nucleotide sequences encoding the glycoproteins gB, gC and gD are known and are accessible from the GenBank database under the accession number AJ004801.

According to the invention, the DNA vaccine against IBR is preferably improved by its formulation with an adjuvant according to the invention, in particular DMRIE, preferably DMRIE-DOPE. Optionally, this may be combined either with the addition of bovine GM-CSF (Maliszewski et al., Molec. Immunol., 1988, 25, 843–850), or the optimization of at least one IBR antigen, or finally the addition of bovine GM-CSF and the optimization of at least one IBR antigen.

A nucleotide sequence encoding bovine GM-CSF is accessible from the GenBank database under the accession number U22385.

The addition of bovine GM-CSF may be carried out by the incorporation of the bovine GM-CSF polypeptide into the vaccinal composition or preferably by the insertion of the nucleotide sequence encoding the bovine GM-CSF into an in vivo expression vector, preferably a plasmid. Preferably, the nucleotide sequence encoding bovine GM-CSF is inserted into a second expression plasmid (e.g. pLF1032 Example 13), different from that (or those) into which the gene(s) encoding the IBR antigen(s) is(are) inserted.

The optimization of the antigens derived from IBR is carried out by substitution, by a "signal" sequence, in particular that of the tPA signal of human origin (GenBank accession number NM_000930), of the sequence of the signal peptide of the glycoprotein gB and/or of the glycoprotein gC and/or of the glycoprotein gD, and/or by the deletion of the DNA fragment encoding the transmembrane domain of gB and/or of gC and/or of gD. The deletion of the DNA fragment encoding the transmembrane domain of one of these glycoproteins is preferably accompanied by the contiguous C-terminal part (cytoplasmic portion of the glycoprotein). The DNA vaccine against IBR according to the invention can therefore encode and express a single optimized IBR antigen (gB, gC or gD) or two of them or all three, that is to say optimized gB, optimized gC and optimized gD.

Nucleotide sequences encoding the BHV-1 antigens which can be used in the present invention and various constructs of expression vectors are given in the accompanying examples and in FR-A1-2751229, in particular in Examples 7 and 8, and in FIGS. 3 and 4.

Preferably, according to the invention, the DNA vaccine against BHV-1 is formulated with DMRIE-DOPE, and is composed of an expression plasmid (e.g. pPB281, Example 3.1.2) encoding the BHV-1 gB antigen optimized by the deletion of the fragment of the nucleotide sequence encoding the transmembrane domain and the contiguous C-terminal part, of a second expression plasmid (e.g. pPB292, Example 3.2.2) encoding the BHV-1 gC antigen optimized by the deletion of the fragment of the nucleotide sequence encoding the transmembrane domain and the contiguous C-terminal part, and of a third expression plasmid (e.g. pPB284, Example 3.3.2) encoding the BHV-1 gD antigen optimized by the deletion of the fragment of the nucleotide sequence encoding the transmembrane domain and the contiguous C-terminal part.

In general, and not only for BHV-1, the C-terminal part contiguous to the sequence encoding the transmembrane domain may be conserved. It is however often easier to delete it at the same time as the sequence encoding the transmembrane domain.

The subject of the present invention is also an improved DNA vaccine capable of inducing an effective and protective immune response in bovines against the bovine respiratory syncitial virus (BRSV).

The BRSV virus is a Paramyxovirus, also a member of the Paramyxoviridae family (Baker et al., Vet. Clin. North Am. Food Anim. Pract., 1997, 13, 425–454). Nucleotide sequences encoding the F protein and the G glycoprotein are known and accessible from the GenBank database respectively under the accession number Y17970 and U33539.

The DNA vaccine against BRSV is preferably formulated with an adjuvant according to the invention, in particular DMRIE, preferably DMRIE-DOPE. This may be optionally combined with either the addition of bovine GM-CSF, or the optimization of at least one BRSV antigen, or finally the addition of bovine GM-CSF and the optimization of at least one BRSV antigen.

The addition of bovine GM-CSF may be carried out as is described for BHV-1.

The optimization of the antigens derived from BRSV is carried out by substitution, by a "signal" sequence, in particular that of the tPA of human origin, of the signal sequence of the F protein of BRSV and/or of the G envelope glycoprotein of BRSV, and/or by the deletion of the DNA fragment encoding the transmembrane domain of F and/or of G. The deletion of the DNA fragment encoding the transmembrane domain of one of these proteins is preferably accompanied by the contiguous C-terminal part. The DNA vaccine against BRSV according to the invention can therefore encode and express a single optimized BRSV antigen (F or G) or both (F and G).

Nucleotide sequences encoding the BRSV antigens which can be used in the present invention and various expression vector constructs are given in the accompanying examples and in FR-A1-2751229, in particular in Examples 9 and 10, and in FIGS. 5 and 6.

Preferably, according to the invention, the DNA vaccine against BRSV is formulated with DMRIE-DOPE, and is composed of an expression plasmid (e.g. pSB114 Example 4.1.3) encoding the F antigen of BRSV optimized by the insertion of the signal sequence of the human tPA in place of the signal sequence of F, by the deletion of the fragment of the nucleotide sequence of F encoding the transmembrane domain and the contiguous C-terminal part, and of a second expression plasmid (e.g. pSB110 Example 4.2.2) encoding the G antigen of BRSV optimized by the insertion of the signal sequence of the human tPA in place of the signal sequence of G, by the deletion of the fragment of the nucleotide sequence encoding the transmembrane domain of G and the contiguous C-terminal part.

The subject of the present invention is also an improved DNA vaccine capable of inducing an effective and protective immune response in bovines against the BVDV virus.

The BVDV virus is a pestivirus of the Flaviviridae family. It is universally distributed in bovine populations and manifests itself by fetal malformations, abortions or clinical respiratory (mucosal disease) and enteric (bovine viral diarrhea) symptoms.

The BVDV viruses are distinguishable by the seriousness of the clinical signs and two groups have been formed, the BVDVs type 1 (inapparent or mild clinical signs) and those of type 2 (acute clinical signs, hemorrhage, high morbidity, high mortality) (Dean H. J. and Leyh R., 1999, Vaccine, 17, 1117–1124).

When a BVDV virus type is not clearly specified, this virus is understood to be type 1 or type 2.

The BVDV virus is an enveloped single-stranded RNA virus composed of a single gene encoding a polyprotein which, after cleavage, gives several well-individualized proteins, in particular the E0 protein (gp48) and the E2 protein (gp53) (Vassilev V. B. et al., 1997, J. Virol., 71, 471–478).

Nucleotide sequences encoding the E0–E2 polyproteins are known and accessible from the GenBank database under the accession number M96687 for BVDV-1 and AF145967 for BVDV-2.

The DNA vaccine against BVDV is preferably formulated with an adjuvant according to the invention, in particular DMRIE, preferably DMRIE-DOPE. This may be optionally combined with either the addition of bovine GM-CSF, or the optimization of at least one BVDV antigen, or finally the addition of bovine GM-CSF and the optimization of at least one BVDV antigen.

The addition of bovine GM-CSF may be carried out as is described for BHV-1.

The optimization of the antigens derived from BVDV is carried out by the addition of a "signal" sequence, in particular that of the tPA of human origin, upstream of the nucleotide sequence encoding the E0 protein of BVDV and/or of the E2 protein of BVDV, and/or by the deletion of the DNA fragment encoding the transmembrane domain of E2, and/or by the insertion of an intron, in particular intron II of the rabbit beta-globin gene upstream of the nucleotide sequence encoding E0 and/or E2. The DNA vaccine against BVDV according to the invention may therefore encode and express a single optimized BVDV antigen (E0 or E2) or both (E0 and E2).

Nucleotide sequences encoding the BVDV antigens which can be used in the present invention and various constructs of expression vectors are given in the accompanying examples and in FR-A1-2751229, in particular in Example 13, and in FIG. 9.

Preferably, according to the invention, the DNA vaccine against BVDV is formulated with DMRIE-DOPE, and is composed of an expression plasmid (e.g. pLF1029 Example 5.1.2, pLF1031 Example 6.2.2) encoding the E0 antigen of BVDV optimized by the insertion of the signal sequence of the human tPA upstream of E0 and by the insertion of intron II of the rabbit beta-globin gene upstream of E0, and of a second expression plasmid (e.g. pLF1021 Example 5.2.2, pLF1023 Example 6.1.2) encoding the E2 antigen of BVDV optimized by the insertion of the signal sequence of the human tPA upstream of E2, by the deletion of the fragment of the nucleotide sequence encoding the transmembrane domain of E2 and the contiguous C-terminal part and by the insertion of intron II of the rabbit beta-globin gene upstream of E2.

A mixture of plasmids can be advantageously produced. The mixture may comprise at least two expression plasmids, each expressing a different immunogen (E0 or E2) and/or obtained from a different type of BVDV (BVDV-1 or BVDV-2). In particular, a mixture made of four plasmids expressing BVDV-1 E0, BVDV-1 E2, BVDV-2 E0 and BVDV-2 E2.

The subject of the present invention is also an improved DNA vaccine capable of inducing an effective and protective immune response in bovines against the parainfluenza virus type 3 (bPI-3).

The bPI-3 virus is a Paramyxovirus, also a member of the Paramyxoviridae family (Tsai et al., Infect. Immun., 1975, 11, 783–803).

Nucleotide sequences encoding the hemagglutinin and neuraminidase proteins (HN) and the fusion protein (F) of bPI-3 are known and accessible from the GenBank database under the accession number U31671.

The DNA vaccine against bPI-3 is preferably formulated with an adjuvant according to the invention, in particular DMRIE, preferably DMRIE-DOPE. This may be optionally combined with either the addition of bovine GM-CSF, or the optimization of at least one bPI-3 antigen, of finally the addition of bovine GM-CSF and the optimization of at least one bPI-3 antigen.

The addition of bovine GM-CSF may be carried out as is described for BHV-1.

The optimization of the antigens derived from bPI-3 is carried out by substitution, by a "signal" sequence, in particular that of the tPA of human origin, of the signal sequence of hemagglutinin-neuraminidase (HN) of bPI-3 and/or of the fusion protein (F) of bPI-3, and/or by the deletion of the DNA fragment encoding the transmembrane domain of HN and/or of F, and/or by the insertion of an intron, in particular of intron II of the rabbit beta-globin gene upstream of the nucleotide sequence encoding HN and/or F. The deletion of the DNA fragment encoding the transmembrane domain of one of these proteins is preferably accompanied by the contiguous C-terminal part. The DNA vaccine against bPI-3 according to the invention may therefore encode and express a single optimized PI-3 antigen (HN or F) or both (HN and F).

Nucleotide sequences encoding the bPI-3 antigens which can be used in the present invention and various expression vector constructs are given in the accompanying examples and in FR-A1-2751229, in particular in Examples 14 and 15, and in FIGS. 10 and 11.

Preferably, according to the invention, the DNA vaccine against bPI-3 is formulated with DMRIE-DOPE, and is composed of an expression plasmid (e.g. pLF1025 Example 7.1.2) encoding the HN antigen of bPI-3 optimized by the insertion of the signal sequence of the human tPA in place of the signal sequence of HN, by the deletion of the fragment of the nucleotide sequence of HN encoding the transmembrane domain and the contiguous C-terminal part and by the insertion of intron II of the rabbit beta-globin gene upstream of HN, and of a second expression plasmid (e.g. pLF1027 Example 7.2.2) encoding the F antigen of bPI-3 optimized by the insertion of the signal sequence of the human tPA in place of the signal sequence of F, by the deletion of the fragment of the nucleotide sequence encoding the transmembrane domain of F and the contiguous C-terminal part and by the insertion of intron II of the rabbit beta-globin gene upstream of F.

The subject of the present invention is an improved DNA vaccine capable of inducing an effective and protective immune response in pigs against porcine herpesvirus (PRV).

The PRV virus is a member of the Alphaherpesvirinae family, this virus is responsible for Aujeszky's disease (Sawitzky D., Arch. Virol. Suppl., 1997, 13, 201–206).

Nucleotide sequences encoding the glycoproteins gB, gC and gD are known and accessible from the GenBank database under the accession number M17321, AF158090, AF086702.

The DNA vaccine against PRV is preferably formulated with an adjuvant according to the invention, in particular DMRIE, preferably DMRIE-DOPE. This may be optionally combined with either the addition of porcine GM-CSF (Inumaru S. and Takamatsu H., Immunol. Cell. Biol., 1995, 73, 474–476), or the optimization of at least one PRV antigen, or finally the addition of porcine GM-CSF and the optimization of at least one PRV antigen.

The addition of porcine GM-CSF may be carried out by the incorporation of the porcine GM-CSF polypeptide into the vaccine composition or by the insertion of a nucleotide sequence encoding the porcine GM-CSF (e.g. accessible from the GenBank database under the accession number D21074) into an in vivo expression vector, preferably a plasmid. Preferably, the nucleotide sequence encoding porcine GM-CSF is inserted into a second expression plasmid (e.g. pLF1033 Example 14), different from that (or those) into which the gene(s) encoding the PRV antigen(s) is (are) inserted.

The optimization of the antigens derived from PRV is carried out by substitution, by a "signal" sequence, in particular that of the tPA signal of human origin (GenBank accession number NM_000930), of the sequence of the signal peptide of the glycoprotein gB and/or of the glycoprotein gC and/or of the glycoprotein gD, and/or by the deletion of the DNA fragment encoding the transmembrane domain of gB and/or of gC and/or of gD. The deletion of the DNA fragment encoding the transmembrane domain of one of these glycoproteins is preferably accompanied by the contiguous C-terminal part. The DNA vaccine against PRV according to the invention may therefore encode and express a single optimized PRV antigen (gB, gC or gD) or two of them or the three, that is to say optimized gB, optimized gC and optimized gD.

Nucleotide sequences encoding the PRV antigens which can be used in the present invention and various expression vector constructs are given in the accompanying examples and in FR-A1-2751224, in particular in Examples 8 and 9 and in FIGS. 3 and 5.

Preferably, according to the invention, the DNA vaccine against PRV is formulated with DMRIE-DOPE, and is composed of an expression plasmid (e.g. pSB102 Example 8.1.2) encoding the gB antigen of PRV optimized by the deletion of the fragement of the nucleotide sequence encoding the transmembrane domain and of the contiguous C-terminal part, of a second expression plasmid (e.g. pSB104 Example 8.2.2) encoding the gC antigen of PRV optimized by the deletion of the fragment of the nucleotide sequence encoding the transmembrane domain and of the contiguous C-terminal part, and of a third expression plasmid (e.g. pSB106 Example 8.3.2) encoding the gD antigen of PRV optimized by the deletion of the fragment of the nucleotide sequence encoding the transmembrane domain and of the contiguous C-terminal part.

The subject of the present invention is an improved DNA vaccine capable of inducing an effective and protective immune response in pigs against the porcine reproductive respiratory syndrome virus (PRRSV).

The PRRSV virus is an Arterivirus, a member of the Arteriviridae family, (Murtaugh et al., Arch. Virol., 1995, 140, 1451–1460).

Nucleotide sequences encoding the proteins encoded by the open reading frames ORF3, ORF5 and ORF6 are known and accessible from the GenBank database under the accession number U87392.

The DNA vaccine against PRRSV is preferably formulated with an adjuvant according to the invention, in particular DMRIE, preferably DMRIE-DOPE. This may be optionally combined with either the addition of porcine GM-CSF, or the optimization of at least one PRRSV antigen, or finally the addition of porcine GM-CSF and the optimization of at least one PRRSV antigen.

The addition of porcine GM-CSF may be carried out as is described for PRV.

The optimization of the antigens derived from PRRSV is carried out by substitution, by a "signal" sequence, in particular that of the tPA signal of human origin (GenBank accession number NM_000930), of the sequence of the signal peptide of the protein encoded by the open reading frame 3 (ORF3, gp45 or large envelope glycoprotein) and/or of the glycoprotein ORF5 (gp25 or envelope glycoprotein E) and/or of the glycoprotein ORF6 (gp18 or membrane protein), and/or by the deletion of the DNA fragment encoding the transmembrane domain of ORF3 and/or ORF5 and/or ORF6. The deletion of the DNA fragment encoding the transmembrane domain of one of these glycoproteins is preferably accompanied by the contiguous C-terminal part. The DNA vaccine against PRRSV according to the invention may therefore encode and express a single optimized PRRSV antigen (ORF3, ORF5 or ORF6) or two of them or the three, that is to say optimized ORF3, optimized ORF5 and optimized ORF6.

Nucleotide sequences encoding the PRRSV antigens which can be used in the present invention and various expression vector constructs are given in the accompanying examples and in FR-A1-2751224, in particular in Examples 14 to 17 and in FIGS. 14 to 17.

Preferably, according to the invention, the DNA vaccine against PRRSV is formulated with DMRIE-DOPE, and is composed of an expression plasmid (e.g. pLF1009 Example 9.1.1, pLF1015 Example 10.1.1) encoding the ORF3 antigen of PRRSV, of a second expression plasmid (e.g. pLF1012 Example 9.2.2, pLF1018 Example 10.2.2) encoding the ORF5 antigen of PRRSV optimized by substitution of the signal sequence of ORF5 by the human tPA signal peptide sequence and by the deletion of the fragment of the nucleotide sequence encoding the transmembrane domain and the contiguous C-terminal part, and of a third expression plasmid (e.g. pLF1014 Example 9.3.2, pLF1016 Example 10.3.2) encoding the ORF6 antigen of PRRSV optimized by the substitution of the signal sequence of ORF6 by the human tPA signal peptide sequence and by the deletion of the fragment of the nucleotide sequence encoding the transmembrane domain and the contiguous C-terminal part.

A mixture of plasmids may be advantageously produced. The mixture may comprise at least two expression plasmids, each expressing a different immunogen (ORF3, ORF5 or ORF6) and/or obtained from a different strain of PRRSV (e.g. European strain, for example Lelystad, American strain ATCC VR-2332). In particular, a mixture made of six plasmids expressing PRRSV Lelystad ORF3, PRRSV Lelystad ORF5, PRRSV Lelystad ORF6, PRRSV VR-2332 ORF3, PRRSV VR-2332 ORF5 and PRRSV VR-2332 ORF6.

The subject of the present invention is also an improved DNA vaccine capable of inducing an effective and protective immune response in porcines against the swine influenza virus (SIV).

The SIV virus is an influenza virus group A, a member of the Orthomyxoviridae family (Murphy B. R. and Webster R. G., Virology, Second Edition, edited by B. N. Fields, D. M. Knipe et al., Raven Press Ltd., New York 1990).

Nucleotide sequences encoding the hemagglutinin (HA) and neuraminidase (NA) proteins of the SIV H1N1 and H3N2 strains are known and accessible from the GenBank database under the accession number K00992, U86145, U07146, AF153238.

The DNA vaccine against SIV is preferably formulated with an adjuvant according to the invention, in particular DMRIE, preferably DMRIE-DOPE. This may be optionally combined with either the addition of porcine GM-CSF, or the optimization of at least one SIV antigen, or finally the addition of porcine GM-CSF and the optimization of at least one SIV antigen.

The addition of porcine GM-CSF may be carried out as is described for PRV.

The optimization of the antigens derived from SIV is carried out by substitution, by a "signal" sequence, in particular that of the tPA of human origin, of the signal sequence of SIV hemagglutinin (HA) and/or of the SIV neuraminidase (NA) protein, and/or by the deletion of the DNA fragment encoding the transmembrane domain of HA and/or of NA, and/or by the insertion of an intron, in particular of intron II of the rabbit beta-globin gene upstream of the nucleotide sequence encoding HA and/or NA. The deletion of the DNA fragment encoding the transmembrane domain of one of these proteins is preferably accompanied by the contiguous C-terminal part. The DNA vaccine against SIV according to the invention may therefore encode and express a single optimized SIV antigen (HA or NA) or both (HA and NA).

Nucleotide sequences encoding SIV antigens which can be used in the present invention and various expression vector constructs are given in the accompanying examples and in FR-A1-2751224, in particular in Examples 10 and 11, and in FIGS. 7 and 9 for SIV stain H1N1, and in Examples 12 and 13, and in FIGS. 11 and 13 for SIV strain H3N2.

Preferably, according to the invention, the DNA vaccine against SIV is formulated with DMRIE-DOPE, and is composed of an expression plasmid (e.g. pLF1002 Example 11.1.2, pLF1006 Example 12.1.2) encoding the HA antigen of SIV optimized by the insertion of the signal sequence of the human tPA in place of the signal sequence of HA, by the deletion of the fragment of the nucleotide sequence of HA encoding the transmembrane domain and the contiguous C-terminal part, and by the insertion of intron II of the rabbit beta-globin gene upstream of HA, and of a second expression plasmid (e.g. pLF1004 Example 11.2.2, pLF1008 Example 12.2.2) encoding the NA antigen of SIV optimized by the insertion of the signal sequence of the human tPA in place of the signal sequence of NA, by the deletion of the fragment of the nucleotide sequence encoding the transmembrane domain of NA and the contiguous C-terminal part, and by the insertion of intron II of the rabbit beta-globin gene upstream of NA.

A mixture of plasmids may be advantageously produced. The mixture may comprise at least two expression plasmids, each expressing a different immunogen (HA or NA) and/or derived from a different SIV strain (e.g. H1N1 or H3N2). In particular, a mixture made of four plasmids expressing SIV H1N1 HA, SIV H1N1 NA, SIV H3N2 HA and SIV H3N2 NA.

Although the invention is described in relation to specific DNA vaccines, the invention and in particular the use of the adjuvants according to the invention also applies to DNA vaccines directed against other pathogens of these animal species.

In the same line of thought, the vaccines according to the invention may be, for an animal species, combined with one another and/or with DNA vaccines directed against other pathogens of the same species.

These other pathogens may be in particular the rabies virus, hog cholera virus and porcine parvoviruses.

An immunogenic preparation or an improved DNA vaccine according to the invention against the rabies virus comprises in particular a plasmid encoding the unmodified G glycoprotein of the rabies virus and DMRIE-DOPE and optionally the addition of GM-CSF.

An improved immunogenic preparation or DNA vaccine according to the invention against the porcine parvovirus comprises in particular a plasmid encoding an antigen derived from the porcine parvovirus (e.g. the VP2 protein, Example 18 and FIG. 18 of FR-A1-2751224) and DMRIE-DOPE and optionally the addition of porcine GM-CSF (e.g. pLF1033, Example 14).

An improved immunogenic preparation or DNA vaccine according to the invention against the hog cholera virus (HCV) comprises in particular a plasmid encoding an antigen derived from HCV (e.g. the E1 protein, Example 19 and FIG. 19 of or the E2 protein, Example 20 and FIG. 20 of the same document) and DMRIE-DOPE and optionally porcine GM-CSF (e.g. pLF1033, Example 14).

Thus, the subject of the present invention is also improved multivalent DNA vaccines which make it possible to obtain an effective protection in bovines against at least two bovine pathogens selected from the group consisting of the BHV-1, BRSV, BVDV, bPI-3 and rabies viruses.

The subject of the present invention is also improved multivalent DNA vaccines which make it possible to obtain effective protection in pigs against at least two porcine pathogens selected from the group consisting of the PRV virus, PRRSV virus, SIV virus, hog cholera virus (or HCV), and porcine parvoviruses.

The multivalent DNA vaccines may be improved by their formulation with an adjuvant according to the invention, in particular with DMRIE, preferably with DMRIE-DOPE. This may be optionally combined either with the addition of GM-CSF as previously described, or with the optimization of at least one antigen of interest as previously described, or finally by the addition of GM-CSF and the optimization of at least one antigen of interest.

The improved multivalent DNA vaccines according to the invention are composed of one or more expression plasmids, such that these vaccines lead to the in vivo expression of at least one immunogen of a first pathogen and of at least one immunogen of at least one other pathogen, infecting the same animal species. At least one of these immunogens is preferably selected from the members of the following group:

F of BRSV, G of BRSV, gB of BHV-1, gC of BHV-1, gD of BHV-1, E0 of BVDV-1, E2 of BVDV-1, E0 of BVDV-2, E2 of BVDV-2, F of bPI-3 and HN of bPI-3 for bovines, and gB of PRV, gC of PRV, gD of PRV, ORF3 of PRRSV strain Lelystad, ORF5 of PRRSV strain Lelystad, ORF6 of PRRSV strain Lelystad, ORF3 of PRRSSV strain VR-2332, ORF5 of PRRSV strain VR-2332, ORF6 of PRRSV strain VR-2332, HA of SIV strain H1N1, NA of SIV strain H1N1, HA of SIV strain H3N2 and NA of SIV strain H3N2 for porcines.

The improved monovalent or multivalent DNA vaccines according to the invention may also be combined with at least one conventional vaccine (inactivated, attenuated live, subunit) or recombinant vaccine using an in vivo expression vector (e.g. poxvirus, adenovirus, herpesvirus) directed against at least one different pathogen infecting the same species.

Persons skilled in the art may refer to FR-A1-2751229 for the methods for constructing the plasmids containing these bovine valencies, to FR-A1-2751224 for the porcine valencies.

The subject of the present invention is also a method of vaccinating farm animals, in particular bovines or porcines. This vaccination method comprises the administration of one of the monovalent or multivalent improved DNA vaccines as described above. These vaccination methods concern gestating females for the passive transfer of immunity or young animals or adults. This vaccination method comprises the administration of one or more doses of the improved DNA vaccine.

The quantity of DNA used in the vaccines according to the present invention is between about 10 μg and about 1000 μg, and preferably between about 50 μg and about 500 μg, for a given plasmid. Persons skilled in the art possess the competence necessary to precisely define the effective dose of DNA to be used for each vaccination protocol.

The dose volumes may be preferably between 0.2 and 5 ml, preferably between 1 and 3 ml.

The improved DNA vaccines according to the invention may be administered, in the context of this vaccination method, by various routes of administration proposed in the prior art for polynucleotide vaccination and by means of known techniques of administration.

According to a preferred mode of the invention, the methods of vaccination comprise the administration of the improved DNA vaccines according to the invention by the intramuscular route, the subcutaneous route or with the aid of an injector without needle by the intradermal route.

The invention will now be described in greater detail with the aid of embodiments taken as nonlimiting examples and referring to the drawings, in which:

FIG. 1: plasmid pVR1012

FIG. 2: plasmid pAB110

SEQUENCE LISTING

SEQ ID NO 1: oligonucleotide PB326
SEQ ID NO 2: oligonucleotide PB329
SEQ ID NO 3: oligonucleotide SB090
SEQ ID NO 4: oligonucleotide SB091
SEQ ID NO 5: oligonucleotide LF001
SEQ ID NO 6: oligonucleotide LF002
SEQ ID NO 7: oligonucleotide PB234
SEQ ID NO 8: oligonucleotide PB235
SEQ ID NO 9: oligonucleotide PB511
SEQ ID NO 10: oligonucleotide PB512
SEQ ID NO 11: oligonucleotide SB221
SEQ ID NO 12: oligonucleotide SB222
SEQ ID NO 13: oligonucleotide PB507
SEQ ID NO 14: oligonucleotide PB508
SEQ ID NO 15: oligonucleotide PB513
SEQ ID NO 16: oligonucleotide PB514
SEQ ID NO 17: oligonucleotide SB223
SEQ ID NO 18: oligonucleotide SB224
SEQ ID NO 19: oligonucleotide PB497
SEQ ID NO 20: oligonucleotide PB498
SEQ ID NO 21: oligonucleotide SB225
SEQ ID NO 22: oligonucleotide SB226
SEQ ID NO 23: oligonucleotide SB210
SEQ ID NO 24: oligonucleotide SB211
SEQ ID NO 25: oligonucleotide SB212
SEQ ID NO 26: oligonucleotide SB220
SEQ ID NO 27: oligonucleotide SB213
SEQ ID NO 28: oligonucleotide SB214
SEQ ID NO 29: oligonucleotide SB215
SEQ ID NO 30: oligonucleotide SB216
SEQ ID NO 31: oligonucleotide LF050
SEQ ID NO 32: oligonucleotide LF051
SEQ ID NO 33: oligonucleotide LF052
SEQ ID NO 34: oligonucleotide LF053
SEQ ID NO 35: oligonucleotide LF039
SEQ ID NO 36: oligonucleotide LF040
SEQ ID NO 37: oligonucleotide LF041
SEQ ID NO 38: oligonucleotide LF042
SEQ ID NO 39: oligonucleotide LF043
SEQ ID NO 40: oligonucleotide LF044
SEQ ID NO 41: oligonucleotide LF045
SEQ ID NO 42: oligonucleotide LF046
SEQ ID NO 43: oligonucleotide LF064
SEQ ID NO 44: oligonucleotide LF065
SEQ ID NO 45: oligonucleotide LF066
SEQ ID NO 46: oligonucleotide LF067
SEQ ID NO 47: oligonucleotide LF047
SEQ ID NO 48: oligonucleotide LF048
SEQ ID NO 49: oligonucleotide LF058
SEQ ID NO 50: oligonucleotide LF059
SEQ ID NO 51: oligonucleotide LF060
SEQ ID NO 52: oligonucleotide LF061
SEQ ID NO 53: oligonucleotide LF062
SEQ ID NO 54: oligonucleotide LF063
SEQ ID NO 55: oligonucleotide SB201
SEQ ID NO 56: oligonucleotide SB202
SEQ ID NO 57: oligonucleotide SB203
SEQ ID NO 58: oligonucleotide SB217
SEQ ID NO 59: oligonucleotide SB204
SEQ ID NO 60: oligonucleotide SB205
SEQ ID NO 61: oligonucleotide SB206
SEQ ID NO 62: oligonucleotide SB218
SEQ ID NO 63: oligonucleotide SB207
SEQ ID NO 64: oligonucleotide SB208
SEQ ID NO 65: oligonucleotide SB209
SEQ ID NO 66: oligonucleotide SB219
SEQ ID NO 67: oligonucleotide LF027
SEQ ID NO 68: oligonucleotide LF028
SEQ ID NO 69: oligonucleotide LF019
SEQ ID NO 70: oligonucleotide LF020
SEQ ID NO 71: oligonucleotide LF021
SEQ ID NO 72: oligonucleotide LF022
SEQ ID NO 73: oligonucleotide LF023
SEQ ID NO 74: oligonucleotide LF024
SEQ ID NO 75: oligonucleotide LF025
SEQ ID NO 76: oligonucleotide LF026
SEQ ID NO 77: oligonucleotide LF037
SEQ ID NO 78: oligonucleotide LF023
SEQ ID NO 79: oligonucleotide LF029
SEQ ID NO 80: oligonucleotide LF030
SEQ ID NO 81: oligonucleotide LF031
SEQ ID NO 82: oligonucleotide LF032
SEQ ID NO 83: oligonucleotide LF033
SEQ ID NO 84: oligonucleotide LF034
SEQ ID NO 85: oligonucleotide LF035
SEQ ID NO 86: oligonucleotide LF036
SEQ ID NO 87: oligonucleotide LF003
SEQ ID NO 88: oligonucleotide LF004
SEQ ID NO 89: oligonucleotide LF005
SEQ ID NO 90: oligonucleotide LF006
SEQ ID NO 91: oligonucleotide LF007
SEQ ID NO 92: oligonucleotide LF008
SEQ ID NO 93: oligonucleotide LF009
SEQ ID NO 94: oligonucleotide LF010
SEQ ID NO 95: oligonucleotide LF011
SEQ ID NO 96: oligonucleotide LF012
SEQ ID NO 97: oligonucleotide LF013
SEQ ID NO 98: oligonucleotide LF014
SEQ ID NO 99: oligonucleotide LF013
SEQ ID NO 100: oligonucleotide LF016
SEQ ID NO 101: oligonucleotide LF017
SEQ ID NO 102: oligonucleotide LF018
SEQ ID NO 103: oligonucleotide LF054
SEQ ID NO 104: oligonucleotide LF055
SEQ ID NO 105: oligonucleotide LF056
SEQ ID NO 106: oligonucleotide LF057

EXAMPLES

For each of the pathogens considered, each gene encoding the principal antigens (native form and modified form) was the subject of a particular construction in a eukaryotic expression plasmid. The secreted forms of the antigens were obtained by deletion of the fragments of genes encoding the transmembrane and cytoplasmic domains. In all cases, the transmembrane domains of the proteins were identified on the basis of the hydropathy profiles (on MacVector 6.5) of the corresponding protein sequences.

Example 1

Molecular Biology Methods 1.1 Extraction of Viral Genomic DNA

Viral suspensions were treated with proteinase K (100 mg/ml final) in the presence of sodium dodecyl sulphate (SDS) (0.5% final) for 2 hours at 37° C. The viral DNA was then extracted with the aid of a phenol/chloroform mixture, and then precipitated with two volumes of absolute ethanol at −20° C. for 16 hours and then centrifuged at 10,000 g for 15 minutes at 4° C. The DNA pellets were dried, and then taken up in a minimum volume of sterile ultrapure water.

1.2 Isolation of Viral Genomic RNA

The genomic RNA of each virus was extracted using the "guanidinium thiocyanate/phenol-chloroform" technique described by P. Chomczynski and N. Sacchi (Anal. Biochem. 1987. 162. 156–159).

1.3 Molecular Biology Techniques

All the constructions of plasmids were carried out using the standard molecular biology techniques described by Sambrook et al. (Molecular Cloning: A Laboratory Manual. 2nd Edition. Cold Spring Harbor Laboratory, Cold Spring Harbor, N.Y., 1989). All the restriction fragments used for the present invention were isolated with the aid of the "Geneclean" kit (BIO101 Inc., La Jolla, Calif. ). For all the constructs, the cloned DNA fragments, as well as the junctions with the expression vector, were sequenced by the Sanger method (Sambrook et al., 1989).

1.4 PCR and RT-PCR

The oligonucleotides specific to the genes or gene fragments cloned were synthesized, some of them containing, in some cases, at their 5' end, restriction sites facilitating the cloning of the amplified fragments. The reverse transcription (RT) reactions and the polymerase chain reaction (PCR) were carried out according to standard techniques (Sambrook et al., 1989).

1.5 Large-scale Purification of Plasmids

The production, on the scale of about ten mg, of purified plasmids entering into the vaccinal compositions was carried out by the caesium chloride-ethidium bromide gradient method (Sambrook et al., 1989).

Example 2

Basic Plasmid Constructs

The eukaryotic expression plasmid pVR1020 (C. J. Luke et al. J. of Infectious Diseases, 1997, 175, 95–97), derived from the plasmid pVR1012 (FIG. 1, FIG. 1 and Example 7 of WO-A-9803199), contains the coding phase of the signal sequence of the human tissue plasminogen activator (tPA).

A plasmid pVR1020 is modified by BamHI-BglII digestion and insertion of a sequence containing several cloning sites (BamHI, NotI, EcoRI, XbaI, PmII, PstI, BglII) and resulting from the pairing of the following oligonucleotides:
PB326 (40 mer) (SEQ ID NO 1) 5' GATCTGCAGCACGT-GTCTAGAGGATATCGAATTCGCGGCC 3' and
PB329 (40 mer) (SEQ ID NO 2) 5' GATCCGCGGCCGC-GAATTCGATATCCTCTAGACACGTGCT 3'.

Figure 2:
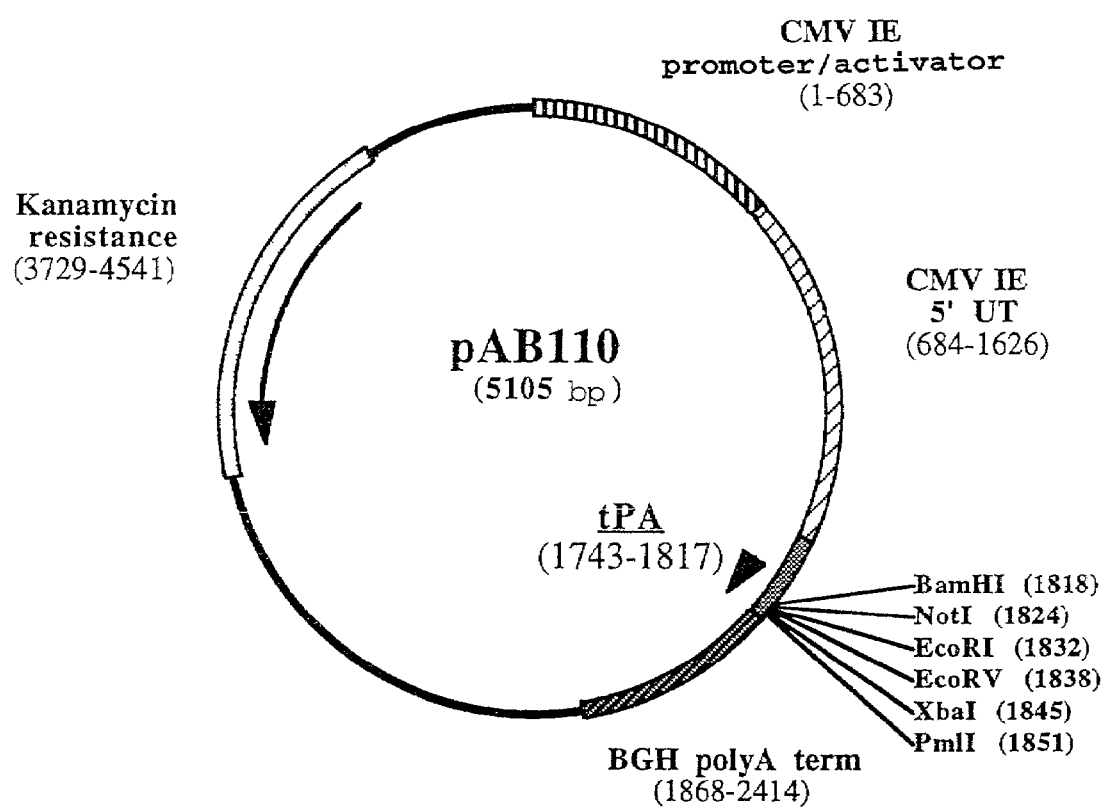

The vector thus obtained, having a size of about 5105 base pairs (or bp), is called pAB110 (FIG. 2).

Intron II of the rabbit β-globin gene is cloned into the vector pCRII (Invitrogen, Carlsbad, Calif., USA) after production of the corresponding DNA fragment by PCR with the aid of the following oligonucleotides:
SB090 (20 mer) (SEQ ID NO 3) 5' TTGGGGACCCTTGAT-TGTTC 3' and
SB091 (21 mer) (SEQ ID NO 4) 5° CTGTAGGAAAAA-GAAGAAGGC 3' using as template the genomic DNA of rabbit peripheral blood cells. The resulting plasmid is designated pNS050.

The expression plasmid pAB110 is modified by introducing the sequence of intron II of the rabbit globin gene into the SalI site situated upstream of the ATG of the signal peptide of tissue plasminogen activator (tPA). The sequence of intron II of the rabbit globin gene is amplified by polymerase chain reaction (PCR) from the plasmid pNS050 using the following oligonucleotide pair:
LF001 (30 mer) (SEQ ID NO 5) 5' CTCCATGTCGACT-TGGGGACCCTTGATTGT 3' and
LF002 (30 mer) (SEQ ID NO 6) 5° CTCCATGTCGACCT-GTAGGAAAAAGAAGAA 3'

The PCR product (573 base pairs or bp) is digested with SalI and cloned into the plasmid pAE110 previously linearized with SalI, to generate the plasmid pLF999 of about 5678 bp.

Example 3

Plasmids Encoding the Various Forms of the Bovine Herpesvirus Type 1 (BHV-1) Antigens Fragments of viral DNA containing the gB, gC and gD genes of the B901 strain of BHV-1 are isolated by digesting the viral genome with various restriction enzymes, by separating them by agarose gel electrophoresis and by analysing them by Southern blotting with the aid of probes corresponding to fragments of the gB, gC and gD genes of the ST strain of BHV-1 (Leung-Tack P. et al., Virology, 1994, 199, 409–421). The BHV-1 Colorado strain [Cooper] (ATCC number VR-864) can also be used. The fragments thus identified are cloned into the vector pBluescript SK+ (Stratagene, La Jolla, Calif., USA) and are at the origin of the clonings of the three genes into the expression vector pVR1012.

3.1 Plasmids Encoding the Various Forms of BHV-1 gB 3.1.1 pPB280: gB Gene (Native Form) Cloned into the Vector pVR1012

Two XhoI-XhoI fragments containing the 5' and 3' portions of the BHV-1 gB gene are identified by Southern blotting and cloned into the vector pBluescript SK+ (Stratagene, La Jolla, Calif., USA) previously digested with XhoI. The plasmids thus obtained are designated pPB128 and pPB117 respectively.

The plasmid pPB128, containing the 5' fragment of the gB gene, is digested with NotI and XhoI, generating a fragment of 1708 bp (fragment A).

The plasmid pPB117, containing the 3' portion of the gB gene, is digested with XhoI and StuI, generating a fragment of 1345 bp. The latter fragment is cloned into the vector pBluescript KS+ (Stratagene, La Jolla, Calif., USA) previously digested with EcoRV and XhoI. The resulting plasmid is called pPB279. The plasmid pPB279 is then digested with XhoI and BamHI, generating a DNA fragment of 1413 bp (fragment B).

Fragments A and B are then cloned into a vector pBluescript KS+ digested with NotI and BamHI, generating plasmid pPB278 (about 6063 bp) and allowing the reconstitution of the BHV-1 gB gene.

The vector pPB278 then serves as template during a PCR reaction carried out with the following oligonucleotides:
PB234 (30 mer) (SEQ ID NO 7) 5' TTGTCGACATGGC-CGCTCGCGGCGGTGCTG 3' and
PB235 (21 mer) (SEQ ID NO 8) 5' GCAGGGCAGCG-GCTAGCGCGG 3'.

The PCR product (146 bp) is then digested with the restriction enzymes SalI and NheI.

The plasmid pPB278 is digested with NheI and BamHI. The fragment of 2728 bp thus obtained and the PCR fragment previously digested are ligated into the vector pVR1012 (Example 2) previously digested with SalI and BamHI, thus generating the plasmid pPB280, having a size of about 7742 bp.

The BHV-1 gB gene encodes a protein of 933 amino acids.

3.1.2 pPB281: gB Gene (Δ[TM-Cter] Form) Cloned into the Vector pVR1012

The truncated form (deleted for its transmembrane (TM) and carboxy-terminal (Cter) domains) of the BHV-1 gB gene is obtained by ligating into the plasmid pVR1012 (Example 2) predigested with SalI and BamHI, both a fragment having a size of 2234 bp obtained after digestion with SalI-PvuII of the plasmid pPB280 (Example 3.1.1) and a fragment of 56 bp obtained by pairing of the following oligonucleotides:
PB511 (52 mer) (SEQ ID NO 9) 5° CTGCACGAGCTC-CGGTTCTACCACATTGACCGCGTGGT-CAAGACGGACTGAG 3' and
PB512 (57 mer) (SEQ ID NO 10) 5' GATCCTCAGTC-CGTCTTGACCACGCGGTCAATGTCGTA-GAACCGGAGCTCGTGCAG 3'.

The plasmid thus generated has a size of about 7154 bp and is called pPB281. The truncated gB gene of BHV-1 encodes a protein of 759 amino acids.

3.1.3 pSB115: gB Gene (tPA Δ[TM-Cter] Form) Cloned into the Vector pAB110

The tPA Δ[TM-Cter] form of the BHV-1 gB gene is amplified by PCR from the template pPB281 (Example 3.1.2) and with the aid of the following primers:
SB221 (39 mer) (SEQ ID NO 11) 5' AAAATTTCGATATC-CGCCGCGGGGCGACCGGCGACAACG 3' and
SB222 (33 mer) (SEQ ID NO 12) 5' GGAAGATCT-TCAGTCCGTCTTGACCACGCGGTC 3'

The amplification product (2088 bp) is digested with the enzymes EcoRV and BglII and cloned into the vector pAB110 (Example 2) previously digested with EcoRV and BglII, generating the plasmid pSB115, having a size of about 7154 bp.

The tPA Δ[TM-Cter] form of the gB gene encodes a glycoprotein of 729 amino acids, containing the extracellular domain of the BHV-1 gB glycoprotein.

3.2. Plasmids Encoding the Various Forms of BHV-1 gC 3.2.1 pPB264: gC Gene (Native Form) Cloned into the Vector pVR1012

A BamHI-HindIII fragment of 3.5 kb containing the complete BHV-1 gC gene is identifed by Southern blotting and cloned into the vector pBluescript SK+. The plasmid thus obtained is called pPB287.

The plasmid pPB287 is then digested with NcoI-BssSI. A digestion fragment having a size of 1492 bp is obtained. It is ligated with a synthetic DNA fragment obtained by the pairing of the following oligonucelotides:

PB507 (37 mer) (SEQ ID NO 13) 5' TCGTGCCTGCG-GCGCAAGGCCCGGGCGCGCCTGTAGT 3' and

PB508 (37 mer) (SEQ ID NO 14) 5° CTAGACTACAG-GCGCGCCCGGGCCTTGCGCCGCAGGC 3', into the plasmid pLitmus 28 (New England Biolabs, Inc., Beverly, Mass., USA) predigested with NcoI and XbaI, generating the intermediate plasmid pPB290.

The fragment of 1554 bp derived from the digestion of pPB290 with PstI and XbaI is cloned into the vector pVR1012 (Example 2) previously digested with PstI and XbaI, thus generating the plasmid pPB264, having a size of about 6427 bp. The BHV-1 gC gene encodes a protein of 508 amino acids.

3.2.2 pPB292: gC Gene (Δ[TM-Cter] Form) Cloned into the Vector pVR1012

The truncated form of the BHV-1 gC gene is obtained by ligating the following three DNA fragments into the vector pVR1012 (Example 2) previously digested with PstI and XbaI:

(a) a fragment of 1035 bp derived from the digestion of pPB264 (Example 3.2.1) with PstI and XhoI, (b) a fragment of 350 bp derived from the digestion of pPB264 with XhoI and BanI and (c) a synthetic fragment of 43 bp resulting from the pairing of the oligonucleotides PB513 and PB514.

These oligonucleotides are the following:

PB513 (43 mer) (SEQ ID NO 15) 5' GCACCGCTGC-CCGAGTTCTCCGCGACCGCCACGTACGACTAGT 3' and PB514 (43 mer) (SEQ ID NO 16) 5' CTAGACTAGTCG-TACGTGGCGGTCGCGGAGAACTCGGGCAGCG 3'.

The plasmid having a size of about 6305 bp thus obtained is called pPB292. The truncated gC gene of BHV-1 encodes a protein of 466 amino acids.

3.2.3 PSB116: gC Gene (tPA Δ[TM-Cter] Form) Cloned into the Vector pAB110

The tPA Δ[TM-Cter] form of the BHV-1 gC gene is amplified by PCR from the template pPB292 (Example 3.2.2) and with the aid of the following primers:

SB223 (39 mer) (SEQ ID NO 17) 5' AAAATTTCGATATC-CCGGCGGGGGCTCGCCGAGGAGGCG 3' and SB224 (32 mer) (SEQ ID NO 18) 5' GGAA-GATCTCTAGTCGTACGTGGCGGTCGCGG 3'

The amplification product (1362 bp) is digested with the enzymes EcoRV and BglII and cloned into the vector pAB110 (Example 2) previously digested with EcoRV and BglII, generating the plasmid pSB116, having a size of about 6404 bp.

The tPA Δ[TM-Cter] form of the gC gene encodes a glycoprotein of 479 amino acids, containing the extracellular domain of the BHV-1 gC glycoprotein.

3.3 Plasmids Encoding the Various Forms of BHV-1 gD 3.3.1 pPB148: gD Gene (Native Form) Cloned into the Vector pVR1012

A XhoI-XhoI fragment of 5 kb containing the BHV-1 gD gene is identified by Southern blotting and cloned into the vector pBluescript SK+ predigested with XhoI, generating the plasmid pPB147.

A fragment of 325 bp derived from the digestion of pPB147 with NdeI and BsrBI and a fragment of 943 bp derived from the digestion of pPB147 with NdeI and StyI are then ligated into the vector pVR1012 (Example 2) predigested with EcoRV and XbaI, thus generating the plasmid pPB148, having a size of about 6171 bp. The BHV-1 gD gene encodes a protein of 417 amino acids.

3.3.2 pPB284: gD Gene (Δ[TM-Cter] Form) Cloned into the Vector pVR1012

The truncated gD gene of BHV-1 is obtained from a fragment obtained after PCR amplification carried out on the genomic DNA of the B901 strain of the BHV-1 virus previously digested with PstI and XbaI and with the aid of the following primer pair:

PB497 (33 mer) (SEQ ID NO 19) 5' TTTCTGCAGATG-CAAGGGCCGACATTGGCCGTG 3' and

PB498 (31 mer) (SEQ ID NO 20) 5' TTTCTAGATT-AGGGCGTAGCGGGGGCGGGCG 3'.

This PCR fragment is then cloned into the plasmid pVR1012 (Example 2) previously digested with PstI and XbaI, generating the plasmid pPB284, having a size of about 5943 bp. The truncated gD gene of BHV-1 encodes a protein of 355 amino acids.

3.3.3 pSB117: gD Gene (tPA Δ[TM-Cter] Form) Cloned into the Vector pAB110

The tPA Δ[TM-Cter] form of the BEHV-1 gD gene is amplified by PCR from the pPB284 template (Example 3.3.2) and with the aid of the following primers:
SB225 (39 mer) (SEQ ID NO 21) 5' AAAATTTCGATATC-CCCCGCGCCGCGGGTGACGGTATAC 3' and
SB226 (33 mer) (SEQ ID NO 22) 5' GGAAGATCTT-TAGGGCGTAGCGGGGGCGGGCGG 3'.

The amplification product (1029 bp) is digested with the enzymes EcoRV and BglII and cloned into the vector pAB110 (Example 2) previously digested with EcoRV and BglII, generating the plasmid pSB117, having a size of about 6071 bp.

The tPA Δ[TM-Cter] form of the gD gene encodes a glycoprotein of 368 amino acids, containing the extracellular domain of the BHV-1 gD glycoprotein.

Example 4

Plasmids Encoding the Various Forms of the Bovine Respiratory Sencitial Virus (BRSV) Antigens The genes encoding the F and G antigens of the BRSV virus are obtained by RT-PCR from the viral RNA of the Snook strain (Thomas et al. Research in Vet. Science, 1982, 33, 170–182). The BRSV A 51908 strain (ATCC number VR-794) may also be used.

4.1 Plasmids Encoding the Various Forms of BRSV-F 4.1.1 pSB107: F Gene (Native Form) Cloned into the Vector pVR1012

The F gene of the Snook strain of BRSV is amplified by RT-PCR using the viral RNA as template and with the aid of the following primers:
SB210 (34 mer) (SEQ ID NO 23) 5' AAATTTTCTGCA-GATGGCGACAACAGCCATGAGG 3' and
SB211 (35 mer) (SEQ ID NO 24) 5' TTAAGGATCCT-CATTTACTAAAGGAAAGATTGTTG 3'.

The amplification product, having a size of 1739 bp, is digested with the enzymes PstI and BamHI and cloned into the vector pVR1012 (Example 2) previously digested with PstI and BamHI, thus generating the plasmid pSB107, having a size of about 6583 bp.

The F gene of the BRSV virus encodes a protein of 574 amino acids.

4.1.2 pSB108: F Gene (0[TM-Cter] Form) Cloned into the Vector pVR1012

The truncated form of the F gene of the Snook strain of BRSV is amplified by RT-PCR using the viral RNA as template and with the aid of the following primers:
SB210 (SEQ ID NO 23) and
SB212 (39 mer) (SEQ ID NO 25) 5' AATTTTGGATCCT-CATGTGGTGGATTTTCCTACATCTAC 3'.

The amplification product (1581 bp) is digested with the enzymes PstI and BamHI and cloned into the vector pVR1012 (Example 2) previously digested with PstI and BamHI, generating the plasmid pSB108, having a size of about 6430 bp.

The truncated form of the F gene encodes a glycoprotein of 523 amino acids, containing the extracellular domain of the BRSV F glycoprotein.

4.1.3 pSB114: F Gene (tPA Δ[TM-Cter] Form) Cloned into the Vector pAB110

The tPA Δ[TM-Cter] form of the F gene of the BRSV Snook strain is amplified by RT-PCR using the viral RNA as template and with the aid of the following primers:
SB212 (SEQ ID NO 25) and
SB220 (38 mer) (SEQ ID NO 26) 5' AAAATTCACGT-GAACATAACAGAAGAATTTTATCAATC 3'.

The amplification product (1516 bp) is digested with the enzymes PmlI and BglII and cloned into the vector pAB110 (Example 2) previously digested with PmlI and BglII, generating the plasmid pSB114, having a size of about 6572 bp.

The tPA Δ[TM-Cter] form of the F gene encodes a glycoprotein of 535 amino acids, containing the extracellular domain of the BRSV F glycoprotein.

4.2 Plasmids Encoding the Various Forms of BRSV-G

In the case of the BRSV G protein (type II glycoprotein), the signal sequence and the transmembrane sequence are indistinguishable, requiring the addition of a signal sequence upstream of the sequence corresponding to the extracellular domain during the deletion of the transmembrane domain.

The plasmid pAB110 (Example 2) is used for the construction of the plasmids containing the truncated forms of the gene encoding the BRSV G protein.

4.2.1 pSB109: G Gene (Native Form) Cloned into the Vector pVR1012

The G gene of the BRSV Snook strain is amplified by RT-PCR using the viral RNA as template and with the aid of the following primers:
SB213 (32 mer) (SEQ ID NO 27) 5' ACGCGTCGACAT-GTCCAACCATACCCATCATC 3' and
SB214 (38 mer) (SEQ ID NO 28) 5' TTAAAATCTA-GATTAGATCTGTGTAGTTGATTGATTTG 3'.

The amplification product (784 bp) is digested with enzymes SalI and XbaI and cloned into the vector pVR1012 (Example 2) previously digested with SalI and XbaI, generating the plasmid pSB109, having a size of about 5661 bp.

The BRSV G gene encodes a glycoprotein of 257 amino acids. 4.2.2 pSB110: G Gene (tPA Δ[TM-Cter] Form) Cloned into the Vector pAB110

The truncated form of the G gene of the BRSV Snook strain is amplified by RT-PCR using the viral RNA as template and with the aid of the following primers:
SB215 (33 mer) (SEQ ID NO 29) 5' TTTTAAGGATC-CGCTAAAGCCAAGCCCACATCC 3' and
SB216 (33 mer) (SEQ ID NO 30) 5' TTAAAATCTA-GATTAGATCTGTGTAGTTGATTG 3'.

The amplification product (666 bp) is digested with the enzymes BamHI and XbaI and cloned into the vector pAB110 (Example 2) previously digested with BamHI and XbaI, generating the plasmid pSB110, having a size of about 5660 bp.

The tPA Δ[TM-Cter] form of the BRSV virus G gene encodes a glycoprotein of 218 amino acids, containing the extracellular domain of the G glycoprotein, but preceded by the signal sequence of the tissue plasminogen activator.

Example 5

Plasmids Encoding the Various Forms of the Bovine Viral Diarrhea Virus Type 1 (BVD-1) Antigens The genes encoding the E0 (glycoprotein of 48 kDa or gp48) and E2 (gp53) antigens of the type 1 BVDV viruses are obtained by RT-PCR from the viral RNA of the Osloss strain (L. De Moerlooze et al. J. Gen. Virol. 1993, 74, 1433–1438; A. Renard et al., DNA, 1985, 4, 439–438; A. Renard et al. Ann. Rech. Vet., 1987, 18, 121–125). The NADL (ATCC VR-534) or New York (ATCC VR-524) strains may also be used.

5.1 Plasmids Encoding the Various Forms of E0 of the BVDV Type 1 Osloss Strain 5.1.1 pLF1028: E0 Gene (Native Form) Cloned into the Vector pVR1012

The complementary DNA (cDNA) of the E0 gene of the Osloss strain is synthesized from the corresponding viral RNA with the aid of the primer LF051 and amplified by the PCR reaction with the aid of the following oligonucleotide pair:

LF050 (36 mer) (SEQ ID NO 31) 5' CATACCGTCGACAT-GAAGAAACTAGAGAAAGCCCTG 3' and

LF051 (40 mer) (SEQ ID NO 32) 5' CATACCGGATCCT-CAGGCTGCATATGCCCCAAACCATGTC 3'.

The DNA fragment of about 765 bp obtained by digesting the PCR product with SalI and BamHI is ligated with a fragment of 4866 bp resulting from the digestion of pVR1012 (Example 2) with SalI and BamHI in order to generate the plasmid pLF1028 (about 5636 bp). The E0 gene of BVDV-1 strain Osloss encodes a protein of 252 amino acids.

An ATG codon is introduced into the sequence of the oligonucleotide LF050 so as to allow the initiation of the translation of the corresponding recombinant E0 polypeptide.

5.1.2 pLF1029: E0 Gene, (β-globin tPA-E0) Form Cloned into the Vector pLF999.

The E0 gene is synthesized by a PCR reaction from the pLF1028 template (Example 5.1.1) and with the aid of the following oligonucleotide pair:

LF052 (39 mer) (SEQ ID NO 33) 5' CATGACGCGGC-CGCTATGAAGAAACTAGAGAAAGCCCTG 3' and LF053 (40 mer) (SEQ ID NO 34) 5' CATGACAGATCTT-TAGGCTGCATATGCCCCAAACCATGTC 3'.

The DNA fragment of about 770 bp obtained by digesting the PCR product with NotI and BglII is ligated with a fragment of 5642 bp resulting from the digestion of pLF999 (Example 2) with NotI and BglII in order to generate the plasmid pLF1029 (about 6417 bp).

The E0 gene of BVDV-1 strain Osloss thus modified (β-globin tPA-E0) encodes a protein of 283 amino acids.

5.2 Plasmids Encoding the Various Forms of E2 of the BVDV Type 1 Osloss Strain 5.2.1 pLF1020: E2 Gene (Native Form) Cloned into the Vector pVR1012

The cDNA of the E2 gene of the Osloss strain is synthesized from the corresponding viral RNA with the aid of the primer LF040 and amplified by a PCR reaction with the aid of the following oligonucleotide pair:

LF039 (33 mer) (SEQ ID NO 35) 5' CATGACGTCGACAT-GACGACTACTGCATTCCTG 3' and

LF040 (36 mer) (SEQ ID NO 36) 5' CATGACAGATCT-TCAACGTCCCGAGGTCATTTGTTC 3'.

The DNA fragment of 1235 bp obtained by digesting the PCR product with SalI and BglII is ligated with a fragment of 4860 bp resulting from the digestion of pVR1012 (Example 2) with SalI and BglII in order to generate the plasmid pLF1020 (about 6100 pb).

The E2 gene of BVDV-1 strain Osloss encodes a protein of 409 amino acids.

An ATG codon is introduced into the sequence of the oligonucleotide LF039 so as to allow the initiation of the translation of the corresponding recombinant E2 polypeptide.

5.2.2 pLF1021: E2 Gene, (β-globin tPA-E2 Δ[TM+Cter]) form Cloned into the Vector pLF999.

The E2 gene deleted for its transmembrane and carboxy-terminal domains is synthesized by a PCR reaction from the pLF1020 template (Example 5.2.1) and with the aid of the following oligonucleotide pair:

LF041 (36 mer) (SEQ ID NO 37) 5' CATGACGCGGC-CGCTATGACGACTACTGCATTCCTG 3' and

LF042 (35 mer) (SEQ ID NO 38) 5' CATGACAGATCT-CAAGCGAAGTAATCCCGGTGGTG 3.

The DNA fragment of 1132 bp obtained by digesting the PCR product with NotI and BglII is ligated with a fragment of 5642 bp resulting from the digestion of pLF999 (Example 2) with NotI and BglII in order to generate the plasmid pLF1021 (about 6779 bp).

The E2 gene of BVDV-1 strain Osloss thus modified (β-globin tPA-E2 Δ[TM+Cter]) encodes a protein of 404 amino acids.

Example 6

Plasmids Encoding the Various Forms of the Bovine Viral Diarrhea Virus Type 2 (BVDV-2) Antigens The genes encoding the E2 antigen (gp53) of the BVDV type 2 viruses are obtained by RT-PCR from the viral RNA of the strain 890 (J. F. Ridpath and S. R. Bolin, Virology, 1995, 212, 36–46). The strain Q140 can also be used and may be obtained from the Quebec Ministry of Agriculture, Fisheries and Food, Armand-Frappier Institute (P. Tijssen et al., Virology, 1996, 217, 356–361). The strains 1373 and 296 may also be used (J. F. Ridpath, BVDV Research Project, National Animal Disease Center, 2300 Dayton Avenue, Ames, USA).

6.1 Plasmids Encoding the Various Forms of E2 of the Type 2—890 Strain 6.1.1. pLF1022: E2 Gene (Native Form) Cloned into the Vector pVR1012

The cDNA of the E2 gene of the strain 890 is synthesized from the corresponding viral RNA with the aid of the primer LF044 amplified by a PCR reaction with the aid of the following oligonucleotide pair:

LF043 (36 mer) (SEQ ID NO 39) 5' ACTGTATCTAGAAT-GACCACCACAGCTTTCCTAATC 3' and

LF044 (39 mer) (SEQ ID NO 40) 5' ACTGTAAGATCTT-TAAGTATTCACTCCAGCACCCATAGC 3'.

The DNA fragment of about 1240 bp obtained by digesting the PCR product with XbaI and BglII is ligated with a fragment of 4891 bp resulting from the digestion of pVR1012 (Example 2) with XbaI and BglII in order to generate the plasmid pLF1022 (about 6136 bp).

The E2 gene of BVDV-2 strain 890 encodes a protein of 410 amino acids.

An ATG codon is introduced into the sequence of the oligonucleotide LF043 so as to allow the initiation of the translation of the corresponding recombinant E2 polypeptide.

6.1.2 pLF1023: E2 Gene, (β-globin tPA-E2 Δ[TM+Cter]) Form, Cloned into the Vector pLF999

The E2 gene deleted for its transmembrane and carboxy-terminal domains is synthesized by a PCR reaction from the pLF1022 template (Example 6.2.1) and with the aid of the following oligonucleotide pair:
LF045 (41 mer) (SEQ ID NO 41) 5' CATGACGCGGC-CGCCCTATGACCACCACAGCTTTCCTAATC 3' and LF046 (36 mer) (SEQ ID NO 42) 5' CATGACAGATCTT-TATATGAACTCTGAGAAGTAGTC 3'.

The DNA fragment of about 1140 bp obtained by digesting the PCR product with NotI and BglII is ligated with a fragment of 5642 bp resulting from the digestion of pLF999 (Example 2) with NotI and BglII in order to generate the plasmid pLF1023 (about 6787 bp).

The E2 gene of BVDV-2 strain 890 thus modified (β-globin tPA-E2 Δ[TM+Cter]) encodes a protein of 405 amino acids.

6.2 Plasmids Encoding the Various Forms of E0 of the Type 2—890 Strain 6.2.1 pLF 1030: E0 Gene (Native Form) Cloned into the Vector pVR1012

The cDNA of the E0 gene of the 890 strain is synthesized from the corresponding viral RNA with the aid of the LF065 primer and amplified by a PCR reaction with the aid of the following oligonucleotide pair:

LF064 (39 mer) (SEQ ID NO 43) 5' CATACCGTCGACAT-GAGAAAGAAATTGGAGAAGGCACTG 3' and LF065 (39 mer) (SEQ ID NO 44) 5' CATACCGGATCCT-CATGCTGCATGAGCACCAAACCATGC 3'.

The DNA fragment of about 768 bp obtained by digesting the PCR product with SalI and BamHI is ligated with a fragment of 4866 bp resulting from the digestion of pVR1012 (Example 2) with SalI and BamHI in order to generate the plasmid pLF1030 (about 5639 bp). The E0 gene of BVDV-2 strain 890 encodes a protein of 253 amino acids.

An ATG codon is introduced into the sequence of the oligonucleotide LF064 so as to allow the initiation of the translation of the corresponding recombinant E0 polypeptide.

6.2.2 pLF1031: E0 Gene, (β-globin tPA-E0) Form, Cloned into the Vector pLF999.

The E0 gene is synthesized by a PCR reaction from the pLF1030 template (Example 6.2.1.) and with the aid of the following oligonucleotide pair:

LF066 (42 mer) (SEQ ID NO 45) 5' CATGACGCGGC-CGCTATGAGAAAGAAATTGGAGAAGGCACTG 3' and LF067 (39 mer) (SEQ ID NO 46) 5' CATACCAGATCT-TCATGCTGCATGAGCACCAAACCATGC 3'.

The DNA fragment of about 770 bp obtained by digesting the PCR product with NotI and BglII is ligated with a fragment of 5642 bp resulting from the digestion of pLF999 (Example 2) with NotI and BglII in order to generate the plasmid pLF1031 (about 6417 bp).

The E0 gene of BVDV-2 strain 890 thus modified (β-globin tPA-E0) encodes a protein of 283 amino acids.

Example 7

Plasmids Encoding the Various Forms of the Bovine Parainfluenza Virus Type 3 (bPI-3) Antigens The genes encoding the hemagglutinin-neuraminidase (HN) and fusion (F) antigens of the bPI-3 virus are obtained by RT-PCR from the viral RNA of the Reisinger SF-4 strain (accessible from ATCC under the number VR-281).

7.1 Plasmids Encoding the Various Forms of HN of the bPI-3 SF-4 Strain 7.1.1 pLF1024: HN Gene (Native Form) Cloned into the Vector pVR1012

The cDNA of the HN gene of the SF-4 strain is synthesized from the corresponding viral RNA with the aid of the primer LF048 and amplified by a PCR reaction with the aid of the following oligonucleotide pair:

LF047 (39 mer) (SEQ ID NO 47) 5' CATATCGTCGA-CATGGAATATTGGAAACACACAAACAGC 3' and LF048 (38 mer) (SEQ ID NO 48) 5' CATGAC-GATATCTAGCTGCAGTTTTTCGGAACTTCTGT 3'.

The DNA fragment of 1726 bp obtained by digesting the PCR product with SalI and EcoRV is ligated with a fragment of 4896 bp resulting from the digestion of pVR1012 (Example 2) with SalI and EcoRV in order to generate the plasmid pLF1024 (about 6619 bp).

The bPI-3 HN gene encodes a protein of 572 amino acids.

7.1.2 pLF1025: HN Gene, (β-globin tPA-E2 Δ[TM]) Form, Cloned into the Vector pLF999

The HN gene deleted for its transmembrane domain is synthesized by a PCR reaction from the pLF1024 template (Example 7.1.1) with the aid of the following oligonucleotide pair:

LF058 (33 mer) (SEQ ID NO 49) 5' CATACTGCGGC-CGCTTTAATTCAAGAGAACAAT 3' and

LF059 (35 mer) (SEQ ID NO 50) 5' CATATC-GATATCTAGCTGCAGTTTTTCGGAACTTC 3'.

The DNA fragment of 1566 bp obtained by digesting the PCR product with NotI and EcoRV is ligated with a fragment of 5663 bp resulting from the digestion of pLF999 (Example 2) with NotI and EcoRV in order to generate the plasmid pLF1025 (about 7229 bp).

The bPI-3 HN gene thus modified (β-globin tPA-E2 Δ[TM]) encodes a protein of 548 amino acids.

7.2 Plasmids Encoding the Various Forms of F of the bPI-3 SF-4 Strain 7.2.1 pLF1026: F Gene (Native Form) Cloned into the Vector pVR1012

The cDNA of the F gene of strain SF-4 is synthesized from the corresponding viral RNA with the aid of the primer LF061 and amplified by a PCR reaction with the aid of the following oligonucleotide pair:

LF060 (36 mer) (SEQ ID NO 51) 5' CATATCGTCGACAT-GATCATCACAAACACAATCATA 3' and

LF061 (36 mer) (SEQ ID NO 52) 5' CATGACCAGATCT-TATTGTCTATTTGTCAGTATATA 3'.

The DNA fragment of 1628 bp obtained by digesting the PCR product with SalI and BglII is ligated with a fragment of 4860 bp resulting from the digestion of pVR1012 (Example 2) with SalI and BglII in order to generate the plasmid pLF1026 (about 6488 bp).

The bPI-3 F gene encodes a protein of 550 amino acids.

7.2.2 pLF1027: F Gene, (β-globin tPA-F Δ[TM+Cter]) Form, Cloned into the Vector pLF999

The F gene deleted for its transmembrane and C-terminal domains is synthesized by a PCR reaction from the pLR1026 template (Example 7.2.1) and with the aid of the following oligonucleotide pair:

LF062 (42 mer) (SEQ ID NO 53) 5' CATACTGCGGC-CGCTCAAATAGACATAACAAAACTGCAACGT 3' and LF063 (41 mer) (SEQ ID NO 54) 5' CATATCGATATCTAT-
GCACTAGATTGATACCAACTTCCAAC 3'.

The DNA fragment of 1434 bp obtained by digesting the PCR product with NotI and EcoRV is ligated with a fragment of 5663 bp resulting from the digestion of pLF999 (Example 2) with NotI and EcoRV in order to generate the plasmid pLF1027 (about 7097 bp).

The bPI-3 F gene thus modified (β-globin tPA-F Δ[TM+Cter]) encodes a protein of 504 amino acids.

Example 8

Plasmids Encoding the Various Forms of the Pseudorabies Virus (PRV) Antigens

The genes encoding the PRV glycoproteins gB, gC and gD are obtained by PCR from the viral DNA of the NIA3 strain (M. Riviere et al. J. Virol. 66, 3424–3434; A. Baskerville et al. The Veterinary Bulletin, 1973, 43 No. 9). Mutants of the PRV NIA3 strain may also be used and are described in U.S. Pat. No. 4,680,176 and deposited with the Collection Nationale de Cultures de Microorganismes (CNCM), Institut Pasteur, Paris, France, under the references I-351 and I-352.

8.1. Plasmids Encoding the Various Forms of PRV-gB 8.1.1. pSB101: gB Gene (Native Form) Cloned into the Vector pVR1012

The gB gene of the PRV NIA3 strain is amplified by PCR using the viral DNA as template and with the aid of the following primers:
SB201 (36 mer) (SEQ ID NO 55) 5' TTTTAAGATATCAT-
GCCCGCTGGTGGCGGTCTTTGG 3' and
SB202 (39 mer) (SEQ ID NO 56) 5' TTTTAAGGATC-
CCTACAGGGCGTCGGGGTCCTCGCTCTC 3'.

The amplification product (2766 bp) is digested with the enzymes EcoRV and BamHI and cloned into the vector pVR1012 (Example 2) previously digested with EcoRV and BamHI, generating the plasmid pSB101, having a size of about 7631 bp.

The PRV gB gene encodes a glycoprotein of 913 amino acids.

8.1.2 pSB102: gB Gene (Δ[TM-Cter] Form) Cloned into the Vector pVR1012

The truncated form of the gB gene of the PRV NIA3 strain is amplified by PCR using the viral DNA as template and with the aid of the following primers:
SB201 (SEQ ID NO 55) and
SB203 (39 mer) (SEQ ID NO 57) 5' TTTTAAGGATC-
CCTAGTGGTCCACCTTGACCACGCGGTC 3'.

The amplification product (2262 bp) is digested with the enzymes EcoRV and BamHI and cloned into the vector pVR1012 (Example 2) previously digested with EcoRV and BamHI, generating the plasmid pSB102, having a size of about 7142 bp.

The truncated form (Δ[TM-Cter]) of the gB gene encodes a glycoprotein of 750 amino acids, containing the extracellular domain of the PRV gB glycoprotein.

8.1.3 pNS009: gB Gene (tPA Δ[TM-Cter] Form) Cloned into the Vector pAB110

The tPA Δ[TM-Cter] form of the gB gene of the PRV NIA3 strain is amplified by PCR from the template pSB101 (Example 8.1.1) and with the aid of the following primers:
SB203 (SEQ ID NO 57) and
SB217 (39 mer) (SEQ ID NO 58) 5' AAAATTTCGATATC-
CACCTCGGCCTCGCCGACGCCCGGG 3'.

The amplification product (2088 bp) is digested with the enzymes EcoRV and BglII and cloned into the vector pAB110 (Example 2) previously digested with EcoRV and BglII, generating the plasmid pNS009, having a size of about 7127 bp.

The tPA Δ[TM-Cter] form of the gB gene encodes a glycoprotein of 720 amino acids, containing the extracellular domain of the PRV gB glycoprotein.

8.2 Plasmids Encoding the Various Forms of PRV-gC 8.2.1 pSB103: gC Gene (Native Form) Cloned into the Vector pVR1012

The gC gene of the PRV NIA3 strain is amplified by PCR using the viral DNA as template and with the aid of the following primers:
SB204 (36 mer) (SEQ ID NO 59) 5' TTTTAAGATAT-
CATGGCCTCGCTCGCGCGTGCGATG 3' and
SB205 (37 mer) (SEQ ID NO 60) 5' TTTTAAAGATCTT-
TAAGGCCCCGCCTGGCGGTAGTAG 3'.

The amplification product (1452 bp) is digested with the enzymes EcoRV and BglII and cloned into the vector pVR1012 (Example 2) previously digested with EcoRV and BglII, generating the plasmid pSB103, having a size of about 6323 bp.

The PRV gC gene encodes a glycoprotein of 479 amino acids.

8.2.2 pSB104: gC Gene (Δ[TM-Cter] Form) Cloned into the Vector pVR1012

The truncated form of the gC gene of the PRV NIA3 strain is amplified by PCR using the viral DNA as template and with the aid of the following primers:
SB204 (SEQ ID NO 59) and
SB206 (36 mer) (SEQ ID NO 61) 5' TTTTAAAGATCTT-
TAGGGGGAGGCGTCGTAGCGCTG 3'.

The amplification product (1332 bp) is digested with the enzymes EcoRV and BglII and cloned into the vector pVR1012 (Example 2) previously digested with EcoRV and BglII, generating the plasmid pSB104, having a size of about 6206 bp.

The truncated form (Δ[TM-Cter]) of the gC gene encodes a glycoprotein of 440 amino acids, containing the extracellular domain of the PRV gC glycoprotein.

8.2.3 pNS012: gC Gene (tPA Δ[TM-Cter] Form) Cloned into the Vector pAB110

The tPA Δ[TM-Cter] form of the gC gene of the PRV NIA3 strain is amplified by PCR from the template pSB103 (Example 8.2.1) and with the aid of the following primers:
SB206 (SEQ ID NO 61) and
SB218 (39 mer) (SEQ ID NO 62) 5' AAAATTTCGATATC-
CACGGCGCTCGGCACGACGCCCAAC 3'.

The amplification product (1270 bp) is digested with the enzymes EcoRV and BglII and cloned into the vector pAB110 (Example 2) previously digested with EcoRV and BglII, generating the plasmid pNS012, having a size of about 6311 bp.

The tPA Δ[TM-Cter] form of the gC gene encodes a glycoprotein of 448 amino acids, containing the extracellular domain of the PRV gC glycoprotein.

8.3 Plasmids Encoding the Various Forms of PRV-gD 8.3.1 pSB105: gD Gene (Native Form) Cloned into the Vector pVR1012

The gD gene of the PRV NIA3 strain is amplified by PCR using the viral DNA as template and with the aid of the following primers:

SB207 (36 mer) (SEQ ID NO 63) 5' AATTTTGATATCAT-GCTGCTCGCAGCGCTATTGGCG 3' and

SB208 (36 mer) (SEQ ID NO 64) 5' AATTTTGGATC-CCTACGGACCGGGCTGCGCTTTTAG 3'.

The amplification product (1227 bp) is digested with the enzymes EcoRV and BamHI and cloned into the vector pVR1012 (Example 2) previously digested with EcoRV and BamHI, generating the plasmid pSB105, having a size of about 6104 bp.

The PRV gD gene encodes a glycoprotein of 404 amino acids.

8.3.2 PSB106: gD Gene (Δ[TM-Cter] form) Cloned into the Vector pVR1012

The truncated form of the gD gene of the PRV NIA3 strain is amplified by PCR using the viral DNA as template and with the aid of the following primers:

SB207 (SEQ ID NO 63) and

SB209 (40 mer) (SEQ ID NO 65) 5' AAATTTTGGATC-CCTAGCGGTGGCGCGAGACGCCCGGCGC 3'.

The amplification product (1077 bp) is digested with the enzymes EcoRV and BamHI and cloned into the vector pVR1012 (Example 2) previously digested with EcoRV and BamHI, generating the plasmid pSB106 having a size of about 5957 bp.

The truncated form (Δ[TM-Cter]) of the gD gene encodes a glycoprotein of 355 amino acids, containing the extracellular domain of the PRV gD glycoprotein.

8.3.3 pPB238: gD Gene (tPA Δ[TM-Cter] Form) Cloned into the Vector pAB110

The tPA Δ[TM-Cter] form of the gD gene of the PRV NIA3 strain is amplified by PCR from the template pSB105 (Example 8.3.1) and with the aid of the following primers:

SB209 (SEQ ID NO 65) and

SB219 (39 mer) (SEQ ID NO 66) 5' AAAATTTCGATATC-CACCTTCCCCCGCCCGCGTACCCG 3'.

The amplification product (1015 bp) is digested with the enzymes EcoRV and BamHI and cloned into the vector pAB110 (Example 2) previously digested with EcoRV and BglII, generating the plasmid pPB238, having a size of about 6056 bp.

The tPA Δ[TM-Cter] form of the gD gene encodes the glycoprotein of 363 amino acids, containing the extracellular domain of the PRV gD glycoprotein.

Example 9

Plasmids Encoding the Various Forms of the Porcine Reproductive Respiratory Syndrome Virus (PRRSV), Strain Lelystad, Antigens The genes encoding the PRRSV ORF3, ORF5 and ORF6 proteins are obtained by RT-PCR from the viral RNA of the Lelystad strain (J. Meulenberg et al. Virology, 1993, 19, 62–72; WO-A-92-21375), deposited Jun. 5, 1991 with the Collection Nationale de Cultures de Microorganismes (CNCM), Institut Pasteur, Paris, France, under the reference I-1102.

9.1 Plasmids Encoding the Various Forms of the PRRSV Lelystad Strain ORF3

9.1.1 pLF1009: ORF3 Gene (Native Form) Cloned into the Vector pVR1012

The cDNA of the ORF3 gene of the Lelystad strain is synthesized from the corresponding viral RNA with the aid of the primer LF028 and amplified by a PCR reaction with the aid of the following oligonucleotide pair:

LF027 (30 mer) (SEQ ID NO 67) 5' CACTACGATATCATGGCTCATCAGTGTGCA 3' and

LF028 (30 mer) (SEQ ID NO 68) 5' CACTACAGATCTTTATCGTGATGTACTGGG 3'.

The DNA fragment of 802 bp obtained by digesting the PCR product with EcoRV and BglIII is ligated with a fragment of 4879 bp resulting from the digestion of pVR1012 (Example 2) with EcoRV and BglIII in order to generate the plasmid pLF1009 having a size of about 5681 bp.

The PRRSV Lelystad ORF3 gene encodes a protein of 265 amino acids.

9.2 Plasmids Encoding the Various Forms of the PRRSV Lelystad Strain ORF5

9.2.1 pLF1011: ORF5 Gene (Native Form) Cloned into the Vector pVR1012

The cDNA of the ORF5 gene of the Lelystad strain is synthesized from the corresponding viral RNA with the aid of the primer LF020 and amplified by a PCR reaction with the aid of the following oligonucleotide pair:

LF019 (30 mer) (SEQ ID NO 69) 5' CTCACCGTCGACATGAGATGTTCTCACAAA 3' and

LF020 (30 mer) (SEQ ID NO 70) 5' CTCACCTCTAGACTAGGCCTCCCATTGCTC 3'.

The DNA fragment of 802 bp obtained by digesting the PCR product with SalI and XbaI is ligated with a fragment of 4879 bp resulting from the digestion of pvR1012 (Example 2) with SalI and XbaI in order to generate the plasmid pLF1011 having a size of about 5681 bp.

The PRRSV Lelystad ORF5 gene encodes a protein of 201 amino acids.

9.2.2 pLF1012: ORF5 Gene (Truncated Form) Cloned into the Vector pAB110

The ORF5 gene deleted for its transmembrane and carboxy-terminal domains is synthesized by a PCR reaction from the template pLF1011 (Example 9.2.1) with the aid of the following oligonucleotide pair:

LF021 (30 mer) (SEQ ID NO 71) 5' CACCTCGGATCCTTTGCCGATGGCAACGGC 3' and

LF022 (33 mer) (SEQ ID NO 72) 5' CACCTCGGATCCTTAGACTTCGGCTTTGCCCAA 3'.

The DNA fragment of 432 bp obtained by digesting the PCR product with BamHI is ligated with a fragment of 5105 bp resulting from the digestion of pAB110 (Example 2) with BamHI in order to generate the plasmid pLF1012 having a size of about 5537 bp.

The PRRSV Lelystad ORF5 gene thus modified (tPA Δ[TM+Cter]) encodes a protein of 168 amino acids.

9.3 Plasmids Encoding the Various Forms of the PRRSV Lelystad Strain ORF6

9.3.1 pLF1013: ORF6 Gene (Native Form) Cloned into the Vector pVR1012

The cDNA of the ORF6 gene of the Lelystad strain is synthesized from the corresponding viral RNA with the aid of the primer LF024 and amplified by a PCR reaction with the aid of the following oligonucleotide pair:

LF023 (30 mer) (SEQ ID NO 73) 5' CACTCAGTCGACATGGGAGGCCTAGACGAT 3' and

LF024 (30 mer) (SEQ ID NO 74) 5' CACTCATCTAGATTACCGGCCATACTTGAC 3'.

The DNA fragment of 528 bp obtained by digesting the PCR product with SalI and XbaI is ligated with the fragment of 4881 bp resulting in the digestion of pVR1012 (Example 2) with SalI and XbaI in order to generate the plasmid pLF1013 having a size of about 5409 bp.

The PRRSV Lelystad ORF6 gene encodes a protein of 173 amino acids.

9.3.2 pLF1014: ORF6 Gene (Truncated Form) Cloned into the Vector pAB110

The ORF6 gene deleted for its transmembrane and carboxy-terminal domains is synthesized by a PCR reaction from the template pLF1013 (Example 9.3.1) with the aid of the following oligonucleotide pair:

LF025 (30 mer) (SEQ ID NO 75) 5' CACTACGGATCCGT-GTCACGCGGCCGACTC 3' and

LF026 (33 mer) (SEQ ID NO 76) 5' CACTACGGATCCT-TAAACAGCTCGTTTGCCGCC 3'.

The DNA fragment of 390 bp obtained by digesting the PCR product with BamHI is ligated with a fragment of 5105 bp resulting from the digestion of pAB110 (Example 2) with BamHI in order to generate the plasmid pLF1014 having a size of about 5495 bp.

The PRRSV Lelystad ORF6 gene thus modified (tPA Δ[TM+Cter]) encodes a protein of 154 amino acids.

Example 10

Plasmids Encoding the Various Forms of the Porcine Reproductive Respiratory Syndrome Virus (PRRSV), American Strain ATCC VR-2332, Antigens The genes encoding the PRRSV virus ORF3, ORF5 and ORF6 proteins are obtained by RT-PCR from the viral RNA of the American strain (M. Murtaugh et al. Arch Virol. 1995, 140, 1451–1460), deposited with the ATCC under the number VR-2332.

10.1 Plasmids Encoding the Various Forms of PRRSV VR-2332 Strain ORF3

10.1.1 pLF1015: ORF3 Gene (Native Form) Cloned into the Vector pVR1012

The cDNA of the ORF3 gene of the VR-2332 strain is synthesized from the corresponding viral RNA with the aid of the primer LF038 and amplified by a PCR reaction with the aid of the following oligonucleotide pair:

LF037 (30 mer) (SEQ ID NO 77) 5' CACTACGATAT-CATGGTTAATAGCTGTACA 3' and

LF038 (30 mer) (SEQ ID NO 78) 5' CACTACTCTAGAC-TATCGCCGTACGGCACT 3'.

The DNA fragment of 769 bp obtained by digesting the PCR product with EcoRV and XbaI is ligated with a fragment of 4900 bp resulting from the digestion of pVR1012 (Example 2) with EcoRV and BglII in order to generate the plasmid pLF1015 having a size of about 5669 bp.

The PRRSV strain VR-2332 ORF3 gene encodes a protein of 254 amino acids.

10.2 Plasmids Encoding the Various Forms of the PRRSV VR-2332 Strain ORF5

10.2.1 pLF1017: ORF5 Gene (Native Form) Cloned into the Vector pVR1012

The cDNA of the ORF5 gene of the VR-2332 strain is synthesized from the corresponding viral RNA with the aid of the primer LF030 and amplified by a PCR reaction with the aid of the following oligonucleotide pair:

LF029 (30 mer) (SEQ ID NO 79) 5' CACTACGATATCAT-GTTGGAGAAATGCTTG 3' and

LF030 (30 mer) (SEQ ID NO 80) 5' CACTACA-GATCTCTAAGGACGACCCCATTG 3'.

The DNA fragment of 607 bp obtained by digesting the PCR product with EcoRV and BglII is ligated with a fragment of 4879 bp resulting from the digestion of pVR1012 (Example 2) with EcoRV and BglII in order to generate the plasmid pLF1017 having a size of about 5486 bp.

The PRRSV strain VR-2332 ORF5 gene encodes a protein of 200 amino acids.

10.2.2 pLF1018: ORF5 Gene (Truncated Form) Cloned into the Vector pAB110

The ORF5 gene deleted for its transmembrane and carboxy-terminal domains is synthesized by a PCR reaction from the template pLF1017 (Example 10.2.1) with the aid of the following oligonucleotide pair:

LF031 (33 mer) (SEQ ID NO 81) 5' CACTACGGATCCGC-CAGCAACGACAGCAGCTCC 3' and

LF032 (33 mer) (SEQ ID NO 82) 5' CACTACGGATCCT-TAGACCTCAACTTTGCCCCT 3'.

The DNA fragment of 426 bp obtained by digesting the PCR product with BamHI is ligated with a fragment of 5105 bp resulting from the digestion of pAB110 (Example 2) with BamHI in order to generate the plasmid pLF1018 having a size of about 5531 bp.

The PRRSV strain VR-2332 ORF5 gene thus modified (tPA Δ[TM+Cter]) encodes a protein of 166 amino acids.

10.3 Plasmids Encoding the Various Forms of the PRRSV VR-2332 Strain ORF6

10.3.1 pLF1019: ORF6 Gene (Native Form) Cloned into the Vector pVR1012

The cDNA of the ORF6 gene of the VR-2332 strain is synthesized from the corresponding viral RNA with the aid of the primer LF034 and amplified by a PCR reaction with the aid of the following oligonucleotide pair:

LF033 (33 mer) (SEQ ID NO 83) 5' CACATCCTGCA-GATGGGGTCGTCCTTAGATGAC 3' and

LF034 (30 mer) (SEQ ID NO 84) 5' CACATCTCTAGAT-TATTTGGCATATTTGAC 3'.

The DNA fragment of 527 bp obtained by digesting the PCR product with PstI and XbaI is ligated with a fragment of 4871 bp resulting from the digestion of pVR1012 (Example 2) with PstI and XbaI in order to generate the plasmid pLF1019 having a size of about 5398 bp.

The PRRSV strain VR-2332 ORF6 gene encodes a protein of 174 amino acids.

10.3.2 pLF1016: ORF6 Gene (Truncated Form) Cloned into the Vector pAB110

The ORF6 gene deleted for its transmembrane and carboxy-terminal domains is synthesized by a PCR reaction from the template pLF1019 (Example 10.3.1) with the aid of the following oligonucleotide pair:

LF035 (30 mer) (SEQ ID NO 85) 5' CACTACGGATCCGT-GAGTCGCGGCCGACTG 3' and

LF036 (33 mer) (SEQ ID NO 86) 5' CACTACGGATCCT-TAAACAGCTTTTCTGCCACC 3'.

The DNA fragment of 390 bp obtained by digesting the PCR product with BamHI is ligated with a fragment of 5105 bp resulting from the digestion of pAB110 (Example 2) with BamHI in order to generate the plasmid pLF1016 having a size of about 5459 bp.

The PRRSV strain VR-2332 ORF6 gene thus modified (tPA Δ[TM+Cter]) encodes a protein of 154 amino acids.

Example 11

Plasmids Encoding the Various Forms of the Swine Influenza Virus (SIV), Strain H1N1, Antigens The genes encoding the hemagglutinin (HA) and neuraminidase (NA) antigens of the swine influenza virus type H1N1 are obtained by RT-PCR from the viral RNA of the "SW" H1N1 strain. Strains are available from the Virology Research Center, Armand-Frappier Institute, University of Quebec, Laval, Canada (D. S. Arora et al., Virus Genes, 1997, 14, 251–254). See also G. W. Both et al., Proc. Natl. Acad. Sci. USA, 1983, 80, 6996–7000.

11.1 Plasmids Encoding the Various Forms of SIV H1N1 Strain HA 11.1.1 pLF1001: HA Gene (Native Form) Cloned into the Vector pVR1012

The cDNA of the HA gene of the H1N1 strain is synthesized from the corresponding viral RNA with the aid of the primer LF004 and amplified by a PCR reaction with the aid of the following oligonucleotide pair:

LF003 (30 mer) (SEQ ID NO 87) 5' CTCCATGATAT-CATGGAAGCAAAACTATTC 3' and

LF004 (30 mer) (SEQ ID NO 88) 5' CTCCATCAGATCT-TAAATGCATATTCTGCA 3'.

The DNA fragment of 1705 bp obtained by digesting the PCR product with EcoRV and BglII is ligated with the fragment of 4879 bp resulting from the digestion of pVR1012 (Example 2) with EcoRV and BglII in order to generate the plasmid pLF1001 having a size of about 6584 bp.

The SIV H1N1 HA gene encodes a protein of 566 amino acids.

11.1.2 pLF1002: HA Gene (Modified Form) Cloned into the Vector pLF999

The HA gene deleted for its transmembrane and carboxy-terminal domains is synthesized by a PCR reaction from the template pLF1001 (Example 11.1.1) with the aid of the following oligonucleotide pair:

LF005 (30 mer) (SEQ ID NO 89) 5' TCCGCGGCCGCA-CATGCTAACAATTCCACA 3' and

LF006 (32 mer) (SEQ ID NO 90) 5' TCCGCGGCCGCT-TACATTGATTCTAGTTTCAC 3'.

The DNA fragment of 1515 bp obtained by digesting the PCR product with NotI is ligated with a fragment of 5678 bp resulting from the digestion of pLF999 (Example 2) with NotI in order to generate the plasmid pLF1002 having a size of 7193 bp.

The SIV H1N1 HA gene thus modified (intron II of the rabit β-globin gene, tPA, Δ[TM+Cter]) encodes a protein of 530 amino acids.

11.2 Plasmids Encoding the Various Forms of the SIV H1N1 Strain NA 11.2.1 PLF1003: NA Gene (Native Form) Cloned into the Vector pVR1012

The cDNA of the NA gene of the H1N1 strain is synthesized from the corresponding viral RNA with the aid of the primer LF008 and amplified by a PCR reaction with the aid of the following oligonucleotide pair:

LF007 (30 mer) (SEQ ID NO 91) 5' CACCTGGTCGA-CATGAATCCAAATCAGAAG 3' and

LF008 (30 mer) (SEQ ID NO 92) 5' CACCTGTCTAGAC-TACTTGTCAATGGTGAA 3'.

The DNA fragment of 1416 bp obtained by digesting the PCR product with SalI and XbaI is ligated with a fragment of 4881 bp resulting from the digestion of pVR1012 (Example 2) with SalI and XbaI in order to generate the plasmid pLF1003 having a size of about 6297 bp.

The SIV H1N1 NA gene encodes a protein of 469 amino acids.

11.2.2 pLF1004: NA Gene (Modified Form) Cloned into the Vector pLF999

The NA gene deleted for its transmembrane and carboxy-terminal domains is synthesized by a PCR reaction from the template pLF1003 with the aid of the following oligonucleotide pair:

LF009 (31 mer) (SEQ ID NO 93) 5' CACTACGAATTCA-CAAATTGGGAATCAAAAT 3' and

LF010 (30 mer) (SEQ ID NO 94) 5' AATTTGTGAAT-TCGCGGCCGCGGATCCGGT 3'.

The DNA fragment of 1207 bp obtained by digesting the PCR product with EcoRI is ligated with a fragment of 5678 bp resulting from the digestion of pLF999 (Example 2) with EcoRI in order to generate the plasmid pLF1004 having a size of about 6885 bp.

The SIV H1N1 NA gene thus modified (intron II of the rabbit β-globin gene, tPA, Δ[TM+Cter]) encodes a protein of 431 amino acids.

Example 12

Plasmids Encoding the Various Forms of the Swine Influenza Virus (SIV), Strain H3N2, Antigens The genes encoding the HA and NA antigens of the type H3N2 swine influenza virus are obtained by RT-PCR from the viral RNA of the "Côtes du Nord 1987" (cdn87) strain referenced by the World Health Organization (WHO) and available from the National Influenza Reference Center, Virology Laboratory, 8 avenue Rockfeller, 69008 Lyon, France.

12.1 Plasmids Encoding the Various Forms of the SIV H3N2 Strain HA 12.1.1 pLF1005: HA Gene (Native Form) Cloned into the Vector pVR1012

The cDNA of the HA gene of the H3N2 strain is synthesized from the corresponding viral RNA with the aid of the primer LF012 and amplified by a PCR reaction with the aid of the following oligonucleotide pair:

LF011 (30 mer) (SEQ ID NO 95) 5' CTGCACGTCGACAT-GAAGACTGTCATTGCC 3' and

LF012 (24 mer)(SEQ ID NO 96) 5' GATATCTCAGATG-CAAATGTTGCA 3'.

The DNA fragment of 1709 bp obtained by digesting the PCR product with EcoRV and SalI is ligated with a fragment of 4893 bp resulting from the digestion of pVR1012 (Example 2) with EcoRV and SalI in order to generate the plasmid pLF1005 having a size of about 6602 bp.

The SIV H3N2 HA gene encodes a protein of 566 amino acids.

12.1.2 pLF1006: HA Gene (Modified Form) Cloned into the Vector pLF999

The HA gene deleted for its transmembrane and carboxy-terminal domains is synthesized by a PCR reaction from the template pLF1005 (Example 12.1.1) with the aid of the following oligonucleotide pair:

LF013 (33 mer) (SEQ ID NO 97) 5' CACCGCGGATCCCT-TCCAGAAAATGGCAGCACA 3' and

LF014 (33 mer) (SEQ ID NO 98) 5' CACCGCGGATCCT-TAGTCTTTGTATCCCGACTT 3'.

The DNA fragment of 1542 bp obtained by digesting the PCR product with BamHI is ligated with a fragment of 5678 bp resulting from the digestion of pLF999 (Example 2) with BamHI in order to generate the plasmid pLF1006 having a size of about 7220 bp.

The SIV H3N2 HA gene thus modified (intron II of the rabbit β-globin gene, tPA, Δ[TM+Cter]) encodes a protein of 538 amino acids.

12.2 Plasmids Encoding the Various Forms of the SIV H3N2 Strain NA 12.2.1 pLF1007: NA Gene (Native Form) Cloned into the Vector pVR1012

The cDNA of the NA gene of the H3N2 strain is synthesized from the corresponding viral RNA with the aid of the primer LF016 and amplified by a PCR reaction with the aid of the following oligonucleotide pair:

LF015 (30 mer) (SEQ ID NO 99) 5' CACTCAGATATCAT-GAATCCAAAGCAAAAG 3' and

LF016 (30 mer) (SEQ ID NO 100) 5' CACTCATCTAGAT-TATATAGGCATGAGATC 3'.

The DNA fragment of 1414 bp obtained by digesting the PCR product with EcoRV and XbaI is ligated with a fragment of 4900 bp resulting from the digestion of pVR1012 (Example 2) with EcoRV and XbaI in order to generate the plasmid pLF1007 having a size of about 6314 bp.

The SIV H3N2 NA gene encodes a protein of 469 amino acids.

12.2.2 pLF1008: NA Gene (Modified Form) Cloned into the Vector pLF999

The NA gene deleted for its transmembrane and carboxy-terminal domains is synthesized by a PCR reaction from the template pLF1005 (Example 12.2.1) with the aid of the following oligonucleotide pair:

LF017 (33 mer) (SEQ ID NO 101) 5' CACTACGGATC-CTTCAAGCAATATGAGTGCGAC 3' and

LF018 (33 mer) (SEQ ID NO 102) 5' CACTACGGATC-CTTATGAAGTCCACCATACTCT 3'.

The DNA fragment of 1221 bp obtained by digesting the PCR product with BamHI is ligated with a fragment of 5678 bp resulting from the digestion of pLF999 (Example 2) with BamHI in order to generate the plasmid pLF1008 having a size of about 6899 bp.

The SIV H3N2 NA gene thus modified (intron II of the rabbit β-globin gene, tPA, Δ[TM+Cter]) encodes a protein of 431 amino acids.

Example 13

Plasmid Encoding Bovine GM-CSF

The cDNA of the bovine GM-CSF gene is synthesized from the cellular RNA of bovine blood mononucleated cells with the aid of the primer LF065 and amplified by a PCR reaction with the aid of the following oligonucleotide pair:

LF054 (36 mer) (SEQ ID NO 103) 5' CATATCGTCGA-CATGTGGCTGCAGAACCTGCTTCTC 3' and

LF055 (34 mer) (SEQ ID NO 104) 5' CATGACCAGATCT-TCACTTCTGGGCTGGTTCCCA 3'.

The DNA fragment of 437 bp obtained by digesting the PCR product with SalI and BglII is ligated with a fragment of 4860 bp resulting from the digestion of pVR1012 (Example 2) with SalI and BglII in order to generate the plasmid pLF1032 (about 5297 bp). The bovine GM-CSF gene encodes a protein of 143 amino acids.

Example 14

Plasmid Encoding Porcine GM-CSF

The cDNA of the porcine GM-CSF gene is synthesized from the cellular RNA of porcine blood mononucleated cells with the aid of the primer LF067 and amplified by a PCR reaction with the aid of the following oligonucleotide pair:

LF056 (36 mer) (SEQ ID NO 105) 5' CATATCGTCGA-CATGTGGCTGCAGAACCTGCTTCTC 3' and

LF057 (37 mer) (SEQ ID NO 106) 5' CATGACCAGATCT-TCACTTCTGGGCTGGTTCCCAGCA 3'.

The DNA fragment of 440 bp obtained by digesting the PCR product with SalI and BglII is ligated with a fragment of 4860 bp resulting from the digestion of pVR1012 (Example 2) with SalI and BglII in order to generate the plasmid pLF1033 (about 5300 bp) The porcine GM-CSF gene encodes a protein of 144 amino acids.

Example 15

Formulation of the Vaccinal Plasmids

The DNA solution containing one or more plasmids according to Examples 3 to 14 is concentrated by ethanolic precipitation as described in Sambrook et al. (1989). The DNA pellet is taken up in a 0.9% NaCl solution so as to obtain a concentration of 1 mg/ml. A 0.75 mM DMRIE-DOPE solution is prepared by taking up a lyophilisate of DMRIE-DOPE with an appropriate volume of sterile $H_2O$.

The formation of the plasmid DNA-lipid complexes is achieved by diluting, in equal parts, the 0.75 mM DMRIE-DOPE solution with the DNA solution at 1 mg/ml in 0.9% NaCl. The DNA solution is gradually introduced, with the aid of a seamed 26 G needle, along the wall of the vial containing the cationic lipid solution so as to avoid the formation of foam. Gentle shaking is carried out as soon as the two solutions have been mixed. A composition comprising 0.375 mM of DMRIE-DOPE and 500 µg/ml of plasmid is finally obtained.

It is desirable for all the solutions used to be at room temperature for all the operations described above. The DNA/DMRIE-DOPE complex formation is allowed to take place at room temperature for 30 minutes before immunizing the animals.

Example 16

Immunization of Bovines Against BHV-1

12 bovines are randomized into 3 groups of 4 s.

Group 1 constitutes the control animal group.

A mixture of vaccinal plasmids pPB281 (encoding BHV-1 gB in a Δ[TM-Cter] form, Example 3.1.2), pPB292 (encoding BHV-1 gC in a Δ[TM-Cter] form, Example 3.2.2) and pPB284 (encoding BHV-1 gD in a Δ[TM-Cter] form, Example 3.3.2) is administered to the animals of Group 2.

The same mixture as that in Group 2, but formulated with DMRIE-DOPE as is described in Example 15, is administered to the animals of Group 3.

An injection of 10 ml, by the intramuscular route, is performed on each bovine with the aid of syringes equipped with needle, and is repeated 21 days later. The total mass of each plasmid used during each immunization is 1500 µg.

Persons skilled in the art possess the necessary competence to adjust the volume or the concentration according to the plasmid dose required.

Monitoring of the serological response induced by the two mixtures of vaccine plasmids expressing the BHV-1 gB, gC and gD antigens is carried out over a period of 35 days after the first vaccination.

The results are presented in the table which follows:

| Plasmids | Formulation | Antigens | Dose | SN at D28 | SN at D35 |
|---|---|---|---|---|---|
| control | — | — | — | 0.2 +/− 0.0 | 0.2 +/− 0.0 |
| pPB281 | — | gB Δ[TM-Cter] | 1500 µg | 1.0 +/− 0.5 | 1.2 +/− 0.8 |
| pPB292 |  | gC Δ[TM-Cter] | 1500 µg |  |  |
| pPB294 |  | gD Δ[TM-Cter] | 1500 µg |  |  |
| pPB281 | DMRIE-DOPE | gB Δ[TM-Cter] | 1500 µg | 2.1 +/− 0.6 | 2.7 +/− 0.6 |
| pPB292 |  | gC Δ[TM-Cter] | 1500 µg |  |  |
| pPB294 |  | gD Δ[TM-Cter] | 1500 µg |  |  |

Example 17

Immunization of Pigs Against PRV 15 pigs, about 7 weeks old, are randomized into 3 groups of 5 animals.

Group 1 constitutes the control animal group.

A mixture of vaccinal plasmids pNS009 (encoding PRV gB in a tPA Δ[TM-Cter] form, Example 8.1.3), pNS012 (encoding PRV gC in a tPA Δ[TM-Cter] form, Example 8.2.3) and pPB238 (encoding PRV gD in a tPA Δ[TM-Cter] form, Example 8.3.3) is administered to the animals of Group 2.

The same mixture as that in Group 3 but formulated with DMRIE-DOPE as is described in Example 15 is administered to the animals of Group 4 so as to obtain a final DMRIE-DOPE concentration of 0.0535 mM.

350 µg of each plasmid necessary for these vaccination protocols are mixed in a final volume of 14 ml.

An injection of 2 ml, by the intramuscular route, is performed with the aid of syringes equipped with needle on each pig, and is repeated 21 days later.

The pigs are challenged at D35 by nasal administration of 2 ml of a solution of PRV strain NIA3 challenge virus in an amount of 1 ml per nostril and having a titre of $10^{7.76}$ CCID$_{50}$ per ml.

Monitoring of the weight (in kg) of each animal is carried out over a period of 42 days after the first vaccination.

ΔG7 (in percentage) corresponds to the difference between the mean percentages of weight growth of a group over a period of 7 days starting on the day of the challenge and expressed relative to one day.

The results are presented in the table which follows:

| Plasmids | Formulation | Antigens | Dose | Mean weight at D35 | Mean weight at D42 | ΔG7 |
|---|---|---|---|---|---|---|
| Control | — | — | — | 25.3 +/− 6.2 | 22.0 +/− 5.0 | — |
| pNS009 | — | gB Δ[TM-Cter]tPA | 350 µg | 25.3 +/− 4.8 | 26.1 +/− 4.7 | 2.46 |
| pNS012 |  | gC Δ[TM-Cter]tPA | 350 µg |  |  |  |
| pPB238 |  | gD Δ[TM-Cter]tPA | 350 µg |  |  |  |
| pNS009 | DMRIE-DOPE | gB Δ[TM-Cter]tPA | 350 µg | 23.8 +/− 4.5 | 26.2 +/− 4.9 | 3.41 |
| pNS012 |  | gC Δ[TM-Cter]tPA | 350 µg |  |  |  |
| pPB238 |  | gD Δ[TM-Cter]tPA | 350 µg |  |  |  |

It should be clearly understood that the invention defined by the appended claims is not limited to the specific embodiments indicated in the description above, but encompasses the variants which depart neither from the scope nor the spirit of the present invention.

The invention claimed is:

1. A DNA vaccine against a bovine pathogen, wherein the bovine pathogen is BRSV, BVDV-1, BVDV-2 or bPI-3, comprising at least one plasmid that contains and expresses in a bovine host cell a nucleotide sequence encoding an immunogen of the bovine pathogen, and a cationic lipid containing a quaternary ammonium salt, of the formula $$R_1-O-CH_2-CH(OR_1)-CH_2-\overset{CH_3}{\underset{CH_3}{N^+}}-R_2-X$$

in which $R_1$ is a saturated or unsaturated linear aliphatic radical having 12 to 18 carbon atoms, $R_2$ is an aliphatic radical containing 2 or 3 carbon atoms, and X a hydroxyl or amine group.

2. The vaccine according to claim 1, further comprising DOPE.

3. The vaccine according to claim 1, further comprising bovine GM-CSF.

4. The vaccine according to claim 2, further comprising bovine GM-CSF.

5. The vaccine according to claim 1, further comprising an expression vector that contains and expresses in a bovine host cell a nucleotide sequence encoding bovine GM-CSF.

6. The vaccine according to claim 2, further comprising an expression vector that contains and expresses in a bovine host cell a nucleotide sequence encoding bovine GM-CSF.

7. The vaccine according to claim 5, wherein the expression vector is a plasmid.

8. The vaccine according to claim 6, wherein the expression vector is a plasmid.

9. The vaccine according to claim 1, wherein the nucleotide sequence encoding the immunogen of the bovine pathogen has deleted therefrom a portion encoding a transmembrane domain.

10. The vaccine according to claim 1, wherein the plasmid further contains and expresses in a bovine host cell a nucleotide sequence encoding a heterologous tPA signal sequence.

11. The vaccine according to claim 1, wherein the plasmid further contains a stabilizing intron.

12. The vaccine according to claim 11, wherein the intron is intron II of a rabbit beta-globin gene.

13. The vaccine according to claim 1, wherein the bovine pathogen is bovine respiratory syncitial virus (BRSV).

14. The vaccine according to claim 13, wherein the immunogen is BRSV F, modified by substitution of the BRSV F signal sequence with a human tPA signal sequence, and/or by deletion of the transmembrane domain.

15. The vaccine according to claim 13, the immunogen is BRSV G, modified by substitution of the BRSV G signal sequence with a human tPA signal sequence, and/or by deletion of the transmembrane domain.

16. The vaccine according to claim 2 comprising a first plasmid that contains and expresses in a bovine host cell a nucleotide sequence encoding bovine respiratory syncitial virus (BRSV) F, modified by substitution of the BRSV F signal sequence with a human tPA signal sequence and deletion of the transmembrane domain and contiguous C-terminal portion; and a second plasmid that contains and expresses in a bovine host cell a nucleotide sequence encoding BRSV G, modified by substitution of the BRSV G signal sequence with a human tPA signal sequence and deletion of the transmembrane domain and contiguous C-terminal portion; and wherein the lipid is DMRIE, whereby the vaccine comprises DMRIE-DOPE.

17. The vaccine according to claim 9, further comprising DOPE.

18. The vaccine according to claim 9, further comprising bovine GM-CSF.

19. The vaccine according to claim 9, further comprising an expression vector that contains and expresses in a bovine host cell a nucleotide sequence encoding bovine GM-CSF.

20. The vaccine according to claim 19, wherein the expression vector is a plasmid.

21. The vaccine according to claim 10, further comprising DOPE.

22. The vaccine according to claim 10, further comprising bovine GM-CSF.

23. The vaccine according to claim 10, further comprising an expression vector that contains and expresses in a bovine host cell a nucleotide sequence encoding bovine GM-CSF.

24. The vaccine according to claim 23, wherein the expression vector is a plasmid.

25. The vaccine according to claim 11, further comprising DOPE.

26. The vaccine according to claim 11, further comprising bovine GM-CSF.

27. The vaccine according to claim 11, further comprising an expression vector tat contains and expresses in a bovine host cell a nucleotide sequence encoding bovine GM-CSF.

28. The vaccine according to claim 27, wherein the expression vector is a plasmid.

29. The vaccine according to claim 13, further comprising DOPE.

30. The vaccine according to claim 13, further comprising bovine GM-CSF.

31. The vaccine according to claim 13, further comprising an expression vector that contains and expresses in a bovine host cell a nucleotide sequence encoding bovine GM-CSF.

32. The vaccine according to claim 31, wherein the expression vector is a plasmid.

33. The vaccine of claim 13 wherein the immunogen is BRSV F.

34. The vaccine of claim 13 wherein the immunogen is BRSV G.

35. The vaccine according to claim 1 or 2 wherein the lipid is DMRIE.

* * * * *

UNITED STATES PATENT AND TRADEMARK OFFICE
CERTIFICATE OF CORRECTION

PATENT NO. : 7,078,388 B2
APPLICATION NO. : 09/760574
DATED : July 18, 2006
INVENTOR(S) : Jean-Christophe Francis Audonnet, Laurent Bernard Fischer and Simona Barzu-Le-Roux It is certified that error appears in the above-identified patent and that said Letters Patent is hereby corrected as shown below:

In the Claims:

Column 72, Claim 27, Line 54    The vaccine according to claim 11, further comprising an expression vector "tat" --that-- contains and expresses in a bovine host cell a nucleotide sequence encoding bovine GM-CSF.

Signed and Sealed this

Seventh Day of November, 2006

JON W. DUDAS
*Director of the United States Patent and Trademark Office*

SEQUENCE LISTING

<160> NUMBER OF SEQ ID NOS: 106

<210> SEQ ID NO 1
<211> LENGTH: 40
<212> TYPE: DNA
<213> ORGANISM: Artificial Sequence
<220> FEATURE:
<223> OTHER INFORMATION: oligonucleotide

<400> SEQUENCE: 1
gatctgcagc acgtgtctag aggatatcga attcgcggcc                                40

<210> SEQ ID NO 2
<211> LENGTH: 40
<212> TYPE: DNA
<213> ORGANISM: Artificial Sequence
<220> FEATURE:
<223> OTHER INFORMATION: oligonucleotide

<400> SEQUENCE: 2
gatccgcggc cgcgaattcg atatcctcta gacacgtgct                                40

<210> SEQ ID NO 3
<211> LENGTH: 20
<212> TYPE: DNA
<213> ORGANISM: Artificial Sequence
<220> FEATURE:
<223> OTHER INFORMATION: oligonucleotide

<400> SEQUENCE: 3
ttggggaccc ttgattgttc                                                      20

<210> SEQ ID NO 4
<211> LENGTH: 21
<212> TYPE: DNA
<213> ORGANISM: Artificial Sequence
<220> FEATURE:
<223> OTHER INFORMATION: oligonucleotide

<400> SEQUENCE: 4
ctgtaggaaa aagaagaagg c                                                    21

<210> SEQ ID NO 5
<211> LENGTH: 30
<212> TYPE: DNA
<213> ORGANISM: Artificial Sequence
<220> FEATURE:
<223> OTHER INFORMATION: oligonucleotide

<400> SEQUENCE: 5
ctccatgtcg acttggggac ccttgattgt                                           30

<210> SEQ ID NO 6
<211> LENGTH: 30
<212> TYPE: DNA
<213> ORGANISM: Artificial Sequence
<220> FEATURE:
<223> OTHER INFORMATION: oligonucleotide

<400> SEQUENCE: 6
ctccatgtcg acctgtagga aaagaagaa                                            30

<210> SEQ ID NO 7
<211> LENGTH: 30

-continued

<212> TYPE: DNA
<213> ORGANISM: Artificial Sequence
<220> FEATURE:
<223> OTHER INFORMATION: oligonucleotide

<400> SEQUENCE: 7
ttgtcgacat ggccgctcgc ggcggtgctg                                      30

<210> SEQ ID NO 8
<211> LENGTH: 21
<212> TYPE: DNA
<213> ORGANISM: Artificial Sequence
<220> FEATURE:
<223> OTHER INFORMATION: oligonucleotide

<400> SEQUENCE: 8
gcagggcagc ggctagcgcg g                                               21

<210> SEQ ID NO 9
<211> LENGTH: 51
<212> TYPE: DNA
<213> ORGANISM: Artificial Sequence
<220> FEATURE:
<223> OTHER INFORMATION: oligonucleotide

<400> SEQUENCE: 9
ctgcacgagc tccggttcta cgacattgac cgctggtcaa gacggactga g              51

<210> SEQ ID NO 10
<211> LENGTH: 56
<212> TYPE: DNA
<213> ORGANISM: Artificial Sequence
<220> FEATURE:
<223> OTHER INFORMATION: oligonucleotide

<400> SEQUENCE: 10
gatcctcagt ccgtcttgac cacgcggtca atgtcgtaga accggagctc gtgcag         56

<210> SEQ ID NO 11
<211> LENGTH: 39
<212> TYPE: DNA
<213> ORGANISM: Artificial Sequence
<220> FEATURE:
<223> OTHER INFORMATION: oligonucleotide

<400> SEQUENCE: 11
aaaatttcga tatccgccgc ggggcgaccg gcgacaacg                            39

<210> SEQ ID NO 12
<211> LENGTH: 33
<212> TYPE: DNA
<213> ORGANISM: Artificial Sequence
<220> FEATURE:
<223> OTHER INFORMATION: oligonucleotide

<400> SEQUENCE: 12
ggaagatctt cagtccgtct tgaccacgcg gtc                                  33

<210> SEQ ID NO 13
<211> LENGTH: 37
<212> TYPE: DNA
<213> ORGANISM: Artificial Sequence
<220> FEATURE:
<223> OTHER INFORMATION: oligonucleotide

<400> SEQUENCE: 13
tcgtgcctgc ggcgcaaggc ccgggcgcgc ctgtagt                               37

<210> SEQ ID NO 14
<211> LENGTH: 37
<212> TYPE: DNA
<213> ORGANISM: Artificial Sequence
<220> FEATURE:
<223> OTHER INFORMATION: oligonucleotide

<400> SEQUENCE: 14
ctagactaca ggcgcgcccg ggccttgcgc cgcaggc                               37

<210> SEQ ID NO 15
<211> LENGTH: 43
<212> TYPE: DNA
<213> ORGANISM: Artificial Sequence
<220> FEATURE:
<223> OTHER INFORMATION: oligonucleotide

<400> SEQUENCE: 15
gcaccgctgc ccgagttctc cgcgaccgcc acgtacgact agt                       43

<210> SEQ ID NO 16
<211> LENGTH: 43
<212> TYPE: DNA
<213> ORGANISM: Artificial Sequence
<220> FEATURE:
<223> OTHER INFORMATION: oligonucleotide

<400> SEQUENCE: 16
ctagactagt cgtacgtggc ggtcgcggag aactcgggca gcg                       43

<210> SEQ ID NO 17
<211> LENGTH: 39
<212> TYPE: DNA
<213> ORGANISM: Artificial Sequence
<220> FEATURE:
<223> OTHER INFORMATION: oligonucleotide

<400> SEQUENCE: 17
aaaatttcga tatcccggcg ggggctcgcc gaggaggcg                            39

<210> SEQ ID NO 18
<211> LENGTH: 32
<212> TYPE: DNA
<213> ORGANISM: Artificial Sequence
<220> FEATURE:
<223> OTHER INFORMATION: oligonucleotide

<400> SEQUENCE: 18
ggaagatctc tagtcgtacg tggcggtcgc gg                                   32

<210> SEQ ID NO 19
<211> LENGTH: 33
<212> TYPE: DNA
<213> ORGANISM: Artificial Sequence
<220> FEATURE:
<223> OTHER INFORMATION: oligonucleotide

<400> SEQUENCE: 19
tttctgcaga tgcaagggcc gacattggcc gtg                                  33

<210> SEQ ID NO 20
<211> LENGTH: 31
<212> TYPE: DNA
<213> ORGANISM: Artificial Sequence

```
<220> FEATURE:
<223> OTHER INFORMATION: oligonucleotide

<400> SEQUENCE: 20
tttctagatt agggcgtagc gggggcgggc g                              31

<210> SEQ ID NO 21
<211> LENGTH: 39
<212> TYPE: DNA
<213> ORGANISM: Artificial Sequence
<220> FEATURE:
<223> OTHER INFORMATION: oligonucleotide

<400> SEQUENCE: 21
aaaatttcga tatccccgc gccgcgggtg acggtatac                       39

<210> SEQ ID NO 22
<211> LENGTH: 33
<212> TYPE: DNA
<213> ORGANISM: Artificial Sequence
<220> FEATURE:
<223> OTHER INFORMATION: oligonucleotide

<400> SEQUENCE: 22
ggaagatctt tagggcgtag cggggggcggg cgg                           33

<210> SEQ ID NO 23
<211> LENGTH: 34
<212> TYPE: DNA
<213> ORGANISM: Artificial Sequence
<220> FEATURE:
<223> OTHER INFORMATION: oligonucleotide

<400> SEQUENCE: 23
aaattttctg cagatggcga caacagccat gagg                           34

<210> SEQ ID NO 24
<211> LENGTH: 35
<212> TYPE: DNA
<213> ORGANISM: Artificial Sequence
<220> FEATURE:
<223> OTHER INFORMATION: oligonucleotide

<400> SEQUENCE: 24
ttaaggatcc tcatttacta aaggaaagat tgttg                          35

<210> SEQ ID NO 25
<211> LENGTH: 39
<212> TYPE: DNA
<213> ORGANISM: Artificial Sequence
<220> FEATURE:
<223> OTHER INFORMATION: oligonucleotide

<400> SEQUENCE: 25
aattttggat cctcatgtgg tggattttcc tacatctac                      39

<210> SEQ ID NO 26
<211> LENGTH: 38
<212> TYPE: DNA
<213> ORGANISM: Artificial Sequence
<220> FEATURE:
<223> OTHER INFORMATION: oligonucleotide

<400> SEQUENCE: 26
aaaattcacg tgaacataac agaagaattt tatcaatc                       38
```

<210> SEQ ID NO 27
<211> LENGTH: 32
<212> TYPE: DNA
<213> ORGANISM: Artificial Sequence
<220> FEATURE:
<223> OTHER INFORMATION: oligonucleotide

<400> SEQUENCE: 27
acgcgtcgac atgtccaacc atacccatca tc                         32

<210> SEQ ID NO 28
<211> LENGTH: 38
<212> TYPE: DNA
<213> ORGANISM: Artificial Sequence
<220> FEATURE:
<223> OTHER INFORMATION: oligonucleotide

<400> SEQUENCE: 28
ttaaaatcta gattagatct gtgtagttga ttgatttg                   38

<210> SEQ ID NO 29
<211> LENGTH: 33
<212> TYPE: DNA
<213> ORGANISM: Artificial Sequence
<220> FEATURE:
<223> OTHER INFORMATION: oligonucleotide

<400> SEQUENCE: 29
ttttaaggat ccgctaaagc caagcccaca tcc                        33

<210> SEQ ID NO 30
<211> LENGTH: 33
<212> TYPE: DNA
<213> ORGANISM: Artificial Sequence
<220> FEATURE:
<223> OTHER INFORMATION: oligonucleotide

<400> SEQUENCE: 30
ttaaaatcta gattagatct gtgtagttga ttg                        33

<210> SEQ ID NO 31
<211> LENGTH: 36
<212> TYPE: DNA
<213> ORGANISM: Artificial Sequence
<220> FEATURE:
<223> OTHER INFORMATION: oligonucleotide

<400> SEQUENCE: 31
cataccgtcg acatgaagaa actagagaaa gccctg                     36

<210> SEQ ID NO 32
<211> LENGTH: 40
<212> TYPE: DNA
<213> ORGANISM: Artificial Sequence
<220> FEATURE:
<223> OTHER INFORMATION: oligonucleotide

<400> SEQUENCE: 32
cataccggat cctcaggctg catatgcccc aaaccatgtc                 40

<210> SEQ ID NO 33
<211> LENGTH: 39
<212> TYPE: DNA
<213> ORGANISM: Artificial Sequence
<220> FEATURE:
<223> OTHER INFORMATION: oligonucleotide

<400> SEQUENCE: 33
catgacgcgg ccgctatgaa gaaactagag aaagccctg         39

<210> SEQ ID NO 34
<211> LENGTH: 40
<212> TYPE: DNA
<213> ORGANISM: Artificial Sequence
<220> FEATURE:
<223> OTHER INFORMATION: oligonucleotide

<400> SEQUENCE: 34
catgacagat ctttaggctg catatgcccc aaaccatgtc        40

<210> SEQ ID NO 35
<211> LENGTH: 33
<212> TYPE: DNA
<213> ORGANISM: Artificial Sequence
<220> FEATURE:
<223> OTHER INFORMATION: oligonucleotide

<400> SEQUENCE: 35
catgacgtcg acatgacgac tactgcattc ctg               33

<210> SEQ ID NO 36
<211> LENGTH: 36
<212> TYPE: DNA
<213> ORGANISM: Artificial Sequence
<220> FEATURE:
<223> OTHER INFORMATION: oligonucleotide

<400> SEQUENCE: 36
catgacagat cttcaacgtc ccgaggtcat ttgttc            36

<210> SEQ ID NO 37
<211> LENGTH: 36
<212> TYPE: DNA
<213> ORGANISM: Artificial Sequence
<220> FEATURE:
<223> OTHER INFORMATION: oligonucleotide

<400> SEQUENCE: 37
catgacgcgg ccgctatgac gactactgca ttcctg            36

<210> SEQ ID NO 38
<211> LENGTH: 35
<212> TYPE: DNA
<213> ORGANISM: Artificial Sequence
<220> FEATURE:
<223> OTHER INFORMATION: oligonucleotide

<400> SEQUENCE: 38
catgacagat ctcaagcgaa gtaatcccgg tggtg             35

<210> SEQ ID NO 39
<211> LENGTH: 36
<212> TYPE: DNA
<213> ORGANISM: Artificial Sequence
<220> FEATURE:
<223> OTHER INFORMATION: oligonucleotide

<400> SEQUENCE: 39
actgtatcta gaatgaccac cacagctttc ctaatc            36

<210> SEQ ID NO 40

```
<210> SEQ ID NO 41
<211> LENGTH: 39
<212> TYPE: DNA
<213> ORGANISM: Artificial Sequence
<220> FEATURE:
<223> OTHER INFORMATION: oligonucleotide

<400> SEQUENCE: 40
actgtaagat ctttaagtat tcactccagc acccatagc                    39

<210> SEQ ID NO 41
<211> LENGTH: 41
<212> TYPE: DNA
<213> ORGANISM: Artificial Sequence
<220> FEATURE:
<223> OTHER INFORMATION: oligonucleotide

<400> SEQUENCE: 41
catgacgcgg ccgccctatg accaccacag ctttcctaat c                 41

<210> SEQ ID NO 42
<211> LENGTH: 36
<212> TYPE: DNA
<213> ORGANISM: Artificial Sequence
<220> FEATURE:
<223> OTHER INFORMATION: oligonucleotide

<400> SEQUENCE: 42
catgacagat ctttatatga actctgagaa gtagtc                       36

<210> SEQ ID NO 43
<211> LENGTH: 39
<212> TYPE: DNA
<213> ORGANISM: Artificial Sequence
<220> FEATURE:
<223> OTHER INFORMATION: oligonucleotide

<400> SEQUENCE: 43
cataccgtcg acatgagaaa gaaattggag aaggcactg                    39

<210> SEQ ID NO 44
<211> LENGTH: 39
<212> TYPE: DNA
<213> ORGANISM: Artificial Sequence
<220> FEATURE:
<223> OTHER INFORMATION: oligonucleotide

<400> SEQUENCE: 44
cataccggat cctcatgctg catgagcacc aaaccatgc                    39

<210> SEQ ID NO 45
<211> LENGTH: 42
<212> TYPE: DNA
<213> ORGANISM: Artificial Sequence
<220> FEATURE:
<223> OTHER INFORMATION: oligonucleotide

<400> SEQUENCE: 45
catgacgcgg ccgctatgag aaagaaattg gagaaggcac tg                42

<210> SEQ ID NO 46
<211> LENGTH: 39
<212> TYPE: DNA
<213> ORGANISM: Artificial Sequence
<220> FEATURE:
<223> OTHER INFORMATION: oligonucleotide

<400> SEQUENCE: 46
```

```
cataccagat cttcatgctg catgagcacc aaaccatgc                    39

<210> SEQ ID NO 47
<211> LENGTH: 39
<212> TYPE: DNA
<213> ORGANISM: Artificial Sequence
<220> FEATURE:
<223> OTHER INFORMATION: oligonucleotide

<400> SEQUENCE: 47
catatcgtcg acatggaata ttggaaacac acaaacagc                    39

<210> SEQ ID NO 48
<211> LENGTH: 38
<212> TYPE: DNA
<213> ORGANISM: Artificial Sequence
<220> FEATURE:
<223> OTHER INFORMATION: oligonucleotide

<400> SEQUENCE: 48
catgacgata tctagctgca gttttttcgga acttctgt                    38

<210> SEQ ID NO 49
<211> LENGTH: 33
<212> TYPE: DNA
<213> ORGANISM: Artificial Sequence
<220> FEATURE:
<223> OTHER INFORMATION: oligonucleotide

<400> SEQUENCE: 49
catactgcgg ccgctttaat tcaagagaac aat                          33

<210> SEQ ID NO 50
<211> LENGTH: 35
<212> TYPE: DNA
<213> ORGANISM: Artificial Sequence
<220> FEATURE:
<223> OTHER INFORMATION: oligonucleotide

<400> SEQUENCE: 50
catatcgata tctagctgca gttttttcgga acttc                       35

<210> SEQ ID NO 51
<211> LENGTH: 36
<212> TYPE: DNA
<213> ORGANISM: Artificial Sequence
<220> FEATURE:
<223> OTHER INFORMATION: oligonucleotide

<400> SEQUENCE: 51
catatcgtcg acatgatcat cacaaacaca atcata                       36

<210> SEQ ID NO 52
<211> LENGTH: 36
<212> TYPE: DNA
<213> ORGANISM: Artificial Sequence
<220> FEATURE:
<223> OTHER INFORMATION: oligonucleotide

<400> SEQUENCE: 52
catgaccaga tcttattgtc tatttgtcag tatata                       36

<210> SEQ ID NO 53
<211> LENGTH: 42
<212> TYPE: DNA
```

```
<213> ORGANISM: Artificial Sequence
<220> FEATURE:
<223> OTHER INFORMATION: oligonucleotide

<400> SEQUENCE: 53
catactgcgg ccgctcaaat agacataaca aaactgcaac gt                    42

<210> SEQ ID NO 54
<211> LENGTH: 41
<212> TYPE: DNA
<213> ORGANISM: Artificial Sequence
<220> FEATURE:
<223> OTHER INFORMATION: oligonucleotide

<400> SEQUENCE: 54
catatcgata tctatgcact agattgatac caacttccaa c                     41

<210> SEQ ID NO 55
<211> LENGTH: 36
<212> TYPE: DNA
<213> ORGANISM: Artificial Sequence
<220> FEATURE:
<223> OTHER INFORMATION: oligonucleotide

<400> SEQUENCE: 55
ttttaagata tcatgcccgc tggtggcggt ctttgg                           36

<210> SEQ ID NO 56
<211> LENGTH: 39
<212> TYPE: DNA
<213> ORGANISM: Artificial Sequence
<220> FEATURE:
<223> OTHER INFORMATION: oligonucleotide

<400> SEQUENCE: 56
ttttaaggat ccctacaggg cgtcggggtc ctcgctctc                        39

<210> SEQ ID NO 57
<211> LENGTH: 39
<212> TYPE: DNA
<213> ORGANISM: Artificial Sequence
<220> FEATURE:
<223> OTHER INFORMATION: oligonucleotide

<400> SEQUENCE: 57
ttttaaggat ccctagtggt ccaccttgac cacgcggtc                        39

<210> SEQ ID NO 58
<211> LENGTH: 39
<212> TYPE: DNA
<213> ORGANISM: Artificial Sequence
<220> FEATURE:
<223> OTHER INFORMATION: oligonucleotide

<400> SEQUENCE: 58
aaaatttcga tatccacctc ggcctcgccg acgcccggg                        39

<210> SEQ ID NO 59
<211> LENGTH: 36
<212> TYPE: DNA
<213> ORGANISM: Artificial Sequence
<220> FEATURE:
<223> OTHER INFORMATION: oligonucleotide

<400> SEQUENCE: 59
ttttaagata tcatggcctc gctcgcgcgt gcgatg                           36
```

<210> SEQ ID NO 60
<211> LENGTH: 37
<212> TYPE: DNA
<213> ORGANISM: Artificial Sequence
<220> FEATURE:
<223> OTHER INFORMATION: oligonucleotide

<400> SEQUENCE: 60
ttttaaagat ctttaaggcc ccgcctggcg gtagtag    37

<210> SEQ ID NO 61
<211> LENGTH: 36
<212> TYPE: DNA
<213> ORGANISM: Artificial Sequence
<220> FEATURE:
<223> OTHER INFORMATION: oligonucleotide

<400> SEQUENCE: 61
ttttaaagat ctttaggggg aggcgtcgta gcgctg    36

<210> SEQ ID NO 62
<211> LENGTH: 39
<212> TYPE: DNA
<213> ORGANISM: Artificial Sequence
<220> FEATURE:
<223> OTHER INFORMATION: oligonucleotide

<400> SEQUENCE: 62
aaaatttcga tatccacggc gctcggcacg acgcccaac    39

<210> SEQ ID NO 63
<211> LENGTH: 36
<212> TYPE: DNA
<213> ORGANISM: Artificial Sequence
<220> FEATURE:
<223> OTHER INFORMATION: oligonucleotide

<400> SEQUENCE: 63
aattttgata tcatgctgct cgcagcgcta ttggcg    36

<210> SEQ ID NO 64
<211> LENGTH: 36
<212> TYPE: DNA
<213> ORGANISM: Artificial Sequence
<220> FEATURE:
<223> OTHER INFORMATION: oligonucleotide

<400> SEQUENCE: 64
aattttggat ccctacggac cgggctgcgc ttttag    36

<210> SEQ ID NO 65
<211> LENGTH: 40
<212> TYPE: DNA
<213> ORGANISM: Artificial Sequence
<220> FEATURE:
<223> OTHER INFORMATION: oligonucleotide

<400> SEQUENCE: 65
aaatttggga tccctagcgg tggcgcgaga cgcccggcgc    40

<210> SEQ ID NO 66
<211> LENGTH: 39
<212> TYPE: DNA
<213> ORGANISM: Artificial Sequence
<220> FEATURE:

-continued

<223> OTHER INFORMATION: oligonucleotide

<400> SEQUENCE: 66
aaaatttcga tatccacctt cccccgccc gcgtacccg         39

<210> SEQ ID NO 67
<211> LENGTH: 30
<212> TYPE: DNA
<213> ORGANISM: Artificial Sequence
<220> FEATURE:
<223> OTHER INFORMATION: oligonucleotide

<400> SEQUENCE: 67
cactacgata tcatggctca tcagtgtgca              30

<210> SEQ ID NO 68
<211> LENGTH: 30
<212> TYPE: DNA
<213> ORGANISM: Artificial Sequence
<220> FEATURE:
<223> OTHER INFORMATION: oligonucleotide

<400> SEQUENCE: 68
cactacagat ctttatcgtg atgtactggg              30

<210> SEQ ID NO 69
<211> LENGTH: 30
<212> TYPE: DNA
<213> ORGANISM: Artificial Sequence
<220> FEATURE:
<223> OTHER INFORMATION: oligonucleotide

<400> SEQUENCE: 69
ctcaccgtcg acatgagatg ttctcacaaa              30

<210> SEQ ID NO 70
<211> LENGTH: 30
<212> TYPE: DNA
<213> ORGANISM: Artificial Sequence
<220> FEATURE:
<223> OTHER INFORMATION: oligonucleotide

<400> SEQUENCE: 70
ctcacctcta gactaggcct cccattgctc              30

<210> SEQ ID NO 71
<211> LENGTH: 30
<212> TYPE: DNA
<213> ORGANISM: Artificial Sequence
<220> FEATURE:
<223> OTHER INFORMATION: oligonucleotide

<400> SEQUENCE: 71
cacctcggat cctttgccga tggcaacggc              30

<210> SEQ ID NO 72
<211> LENGTH: 33
<212> TYPE: DNA
<213> ORGANISM: Artificial Sequence
<220> FEATURE:
<223> OTHER INFORMATION: oligonucleotide

<400> SEQUENCE: 72
cacctcggat ccttagactt cggctttgcc caa           33

```
<210> SEQ ID NO 73
<211> LENGTH: 30
<212> TYPE: DNA
<213> ORGANISM: Artificial Sequence
<220> FEATURE:
<223> OTHER INFORMATION: oligonucleotide

<400> SEQUENCE: 73
cactcagtcg acatgggagg cctagacgat                                          30

<210> SEQ ID NO 74
<211> LENGTH: 30
<212> TYPE: DNA
<213> ORGANISM: Artificial Sequence
<220> FEATURE:
<223> OTHER INFORMATION: oligonucleotide

<400> SEQUENCE: 74
cactcatcta gattaccggc catacttgac                                          30

<210> SEQ ID NO 75
<211> LENGTH: 30
<212> TYPE: DNA
<213> ORGANISM: Artificial Sequence
<220> FEATURE:
<223> OTHER INFORMATION: oligonucleotide

<400> SEQUENCE: 75
cactacggat ccgtgtcacg cggccgactc                                          30

<210> SEQ ID NO 76
<211> LENGTH: 33
<212> TYPE: DNA
<213> ORGANISM: Artificial Sequence
<220> FEATURE:
<223> OTHER INFORMATION: oligonucleotide

<400> SEQUENCE: 76
cactacggat ccttaaacag ctcgtttgcc gcc                                      33

<210> SEQ ID NO 77
<211> LENGTH: 30
<212> TYPE: DNA
<213> ORGANISM: Artificial Sequence
<220> FEATURE:
<223> OTHER INFORMATION: oligonucleotide

<400> SEQUENCE: 77
cactacgata tcatggttaa tagctgtaca                                          30

<210> SEQ ID NO 78
<211> LENGTH: 30
<212> TYPE: DNA
<213> ORGANISM: Artificial Sequence
<220> FEATURE:
<223> OTHER INFORMATION: oligonucleotide

<400> SEQUENCE: 78
cactactcta gactatcgcc gtacggcact                                          30

<210> SEQ ID NO 79
<211> LENGTH: 30
<212> TYPE: DNA
<213> ORGANISM: Artificial Sequence
<220> FEATURE:
<223> OTHER INFORMATION: oligonucleotide
```

```
<400> SEQUENCE: 79
cactacgata tcatgttgga gaaatgcttg                                30

<210> SEQ ID NO 80
<211> LENGTH: 30
<212> TYPE: DNA
<213> ORGANISM: Artificial Sequence
<220> FEATURE:
<223> OTHER INFORMATION: oligonucleotide

<400> SEQUENCE: 80
cactacagat ctctaaggac gaccccattg                                30

<210> SEQ ID NO 81
<211> LENGTH: 33
<212> TYPE: DNA
<213> ORGANISM: Artificial Sequence
<220> FEATURE:
<223> OTHER INFORMATION: oligonucleotide

<400> SEQUENCE: 81
cactacggat ccgccagcaa cgacagcagc tcc                            33

<210> SEQ ID NO 82
<211> LENGTH: 33
<212> TYPE: DNA
<213> ORGANISM: Artificial Sequence
<220> FEATURE:
<223> OTHER INFORMATION: oligonucleotide

<400> SEQUENCE: 82
cactacggat ccttagacct caactttgcc cct                            33

<210> SEQ ID NO 83
<211> LENGTH: 33
<212> TYPE: DNA
<213> ORGANISM: Artificial Sequence
<220> FEATURE:
<223> OTHER INFORMATION: oligonucleotide

<400> SEQUENCE: 83
cacatcctgc agatggggtc gtccttagat gac                            33

<210> SEQ ID NO 84
<211> LENGTH: 30
<212> TYPE: DNA
<213> ORGANISM: Artificial Sequence
<220> FEATURE:
<223> OTHER INFORMATION: oligonucleotide

<400> SEQUENCE: 84
cacatctcta gattatttgg catatttgac                                30

<210> SEQ ID NO 85
<211> LENGTH: 30
<212> TYPE: DNA
<213> ORGANISM: Artificial Sequence
<220> FEATURE:
<223> OTHER INFORMATION: oligonucleotide

<400> SEQUENCE: 85
cactacggat ccgtgagtcg cggccgactg                                30

<210> SEQ ID NO 86
<211> LENGTH: 33
```

<212> TYPE: DNA
<213> ORGANISM: Artificial Sequence
<220> FEATURE:
<223> OTHER INFORMATION: oligonucleotide

<400> SEQUENCE: 86
cactacggat ccttaaacag cttttctgcc acc                                    33

<210> SEQ ID NO 87
<211> LENGTH: 30
<212> TYPE: DNA
<213> ORGANISM: Artificial Sequence
<220> FEATURE:
<223> OTHER INFORMATION: oligonucleotide

<400> SEQUENCE: 87
ctccatgata tcatggaagc aaaactattc                                        30

<210> SEQ ID NO 88
<211> LENGTH: 30
<212> TYPE: DNA
<213> ORGANISM: Artificial Sequence
<220> FEATURE:
<223> OTHER INFORMATION: oligonucleotide

<400> SEQUENCE: 88
ctccatcaga tcttaaatgc atattctgca                                        30

<210> SEQ ID NO 89
<211> LENGTH: 30
<212> TYPE: DNA
<213> ORGANISM: Artificial Sequence
<220> FEATURE:
<223> OTHER INFORMATION: oligonucleotide

<400> SEQUENCE: 89
tccgcggccg cacatgctaa caattccaca                                        30

<210> SEQ ID NO 90
<211> LENGTH: 32
<212> TYPE: DNA
<213> ORGANISM: Artificial Sequence
<220> FEATURE:
<223> OTHER INFORMATION: oligonucleotide

<400> SEQUENCE: 90
tccgcggccg cttacattga ttctagtttc ac                                     32

<210> SEQ ID NO 91
<211> LENGTH: 30
<212> TYPE: DNA
<213> ORGANISM: Artificial Sequence
<220> FEATURE:
<223> OTHER INFORMATION: oligonucleotide

<400> SEQUENCE: 91
cacctggtcg acatgaatcc aaatcagaag                                        30

<210> SEQ ID NO 92
<211> LENGTH: 30
<212> TYPE: DNA
<213> ORGANISM: Artificial Sequence
<220> FEATURE:
<223> OTHER INFORMATION: oligonucleotide

<400> SEQUENCE: 92

-continued cacctgtcta gactacttgt caatggtgaa                              30

<210> SEQ ID NO 93
<211> LENGTH: 31
<212> TYPE: DNA
<213> ORGANISM: Artificial Sequence
<220> FEATURE:
<223> OTHER INFORMATION: oligonucleotide

<400> SEQUENCE: 93
cactacgaat tcacaaattg ggaatcaaaa t                            31

<210> SEQ ID NO 94
<211> LENGTH: 30
<212> TYPE: DNA
<213> ORGANISM: Artificial Sequence
<220> FEATURE:
<223> OTHER INFORMATION: oligonucleotide

<400> SEQUENCE: 94
aatttgtgaa ttcgcggccg cggatccggt                              30

<210> SEQ ID NO 95
<211> LENGTH: 30
<212> TYPE: DNA
<213> ORGANISM: Artificial Sequence
<220> FEATURE:
<223> OTHER INFORMATION: oligonucleotide

<400> SEQUENCE: 95
ctgcacgtcg acatgaagac tgtcattgcc                              30

<210> SEQ ID NO 96
<211> LENGTH: 24
<212> TYPE: DNA
<213> ORGANISM: Artificial Sequence
<220> FEATURE:
<223> OTHER INFORMATION: oligonucleotide

<400> SEQUENCE: 96
gatatctcag atgcaaatgt tgca                                    24

<210> SEQ ID NO 97
<211> LENGTH: 33
<212> TYPE: DNA
<213> ORGANISM: Artificial Sequence
<220> FEATURE:
<223> OTHER INFORMATION: oligonucleotide

<400> SEQUENCE: 97
caccgcggat cccttccaga aaatggcagc aca                          33

<210> SEQ ID NO 98
<211> LENGTH: 33
<212> TYPE: DNA
<213> ORGANISM: Artificial Sequence
<220> FEATURE:
<223> OTHER INFORMATION: oligonucleotide

<400> SEQUENCE: 98
caccgcggat ccttagtctt tgtatcccga ctt                          33

<210> SEQ ID NO 99
<211> LENGTH: 30
<212> TYPE: DNA
<213> ORGANISM: Artificial Sequence

```
<220> FEATURE:
<223> OTHER INFORMATION: oligonucleotide

<400> SEQUENCE: 99
cactcagata tcatgaatcc aaagcaaaag                                30

<210> SEQ ID NO 100
<211> LENGTH: 30
<212> TYPE: DNA
<213> ORGANISM: Artificial Sequence
<220> FEATURE:
<223> OTHER INFORMATION: oligonucleotide

<400> SEQUENCE: 100
cactcatcta gattatatag gcatgagatc                                30

<210> SEQ ID NO 101
<211> LENGTH: 33
<212> TYPE: DNA
<213> ORGANISM: Artificial Sequence
<220> FEATURE:
<223> OTHER INFORMATION: oligonucleotide

<400> SEQUENCE: 101
cactacggat ccttcaagca atatgagtgc gac                            33

<210> SEQ ID NO 102
<211> LENGTH: 33
<212> TYPE: DNA
<213> ORGANISM: Artificial Sequence
<220> FEATURE:
<223> OTHER INFORMATION: oligonucleotide

<400> SEQUENCE: 102
cactacggat ccttatgaag tccaccatac tct                            33

<210> SEQ ID NO 103
<211> LENGTH: 36
<212> TYPE: DNA
<213> ORGANISM: Artificial Sequence
<220> FEATURE:
<223> OTHER INFORMATION: oligonucleotide

<400> SEQUENCE: 103
catatcgtcg acatgtggct gcagaacctg cttctc                         36

<210> SEQ ID NO 104
<211> LENGTH: 34
<212> TYPE: DNA
<213> ORGANISM: Artificial Sequence
<220> FEATURE:
<223> OTHER INFORMATION: oligonucleotide

<400> SEQUENCE: 104
catgaccaga tcttcacttc tgggctggtt ccca                           34

<210> SEQ ID NO 105
<211> LENGTH: 36
<212> TYPE: DNA
<213> ORGANISM: Artificial Sequence
<220> FEATURE:
<223> OTHER INFORMATION: oligonucleotide

<400> SEQUENCE: 105
catatcgtcg acatgtggct gcagaacctg cttctc                         36
```

```
<210> SEQ ID NO 106
<211> LENGTH: 37
<212> TYPE: DNA
<213> ORGANISM: Artificial Sequence
<220> FEATURE:
<223> OTHER INFORMATION: oligonucleotide

<400> SEQUENCE: 106
catgaccaga tcttcacttc tgggctggtt cccagca                              37
```